United States Patent [19]

Hannah

[11] 4,283,397
[45] Aug. 11, 1981

[54] 7-N-HETEROCYCLYL CEPHALOSPORINS AND ANTIBIOTIC PHARMACEUTICAL COMPOSITIONS CONTAINING THEM

[75] Inventor: John Hannah, Matawan, N.J.

[73] Assignee: Merck & Co., Inc., Rahway, N.J.

[21] Appl. No.: 62,836

[22] Filed: Aug. 1, 1979

[51] Int. Cl.³ .................. A61K 31/545; C07D 501/14
[52] U.S. Cl. ...................................... 424/246; 544/21; 544/22; 544/25; 544/27; 544/28; 546/13; 546/346; 546/343; 546/341; 546/283
[58] Field of Search ...................... 544/21, 22, 25, 27, 544/28; 424/246

[56] References Cited
U.S. PATENT DOCUMENTS

| | | | |
|---|---|---|---|
| 3,646,024 | 2/1972 | Holdrege et al. | 544/28 X |
| 3,821,198 | 6/1974 | Lee et al. | 544/28 X |
| 3,929,779 | 12/1975 | Bickel et al. | 544/27 |
| 3,957,764 | 5/1976 | Lund | 542/419 |
| 4,042,585 | 8/1977 | Koppel | 544/22 |
| 4,092,474 | 5/1978 | Yoshioka et al. | 544/17 |
| 4,168,309 | 9/1979 | Ayres | 544/22 X |

Primary Examiner—Donald G. Daus
Assistant Examiner—Diana G. Rivers
Attorney, Agent, or Firm—Frank M. Mahon; Hesna J. Pfeiffer

[57] ABSTRACT

Disclosed are antibiotic cephalosporins (I) of the formula:

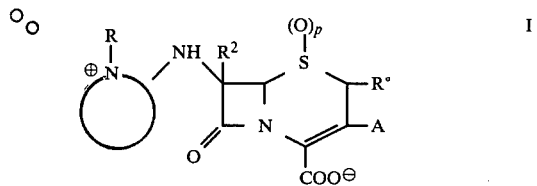

wherein the stylized radical attached to the 7-amino nitrogen of the cephalosporin moiety represents a nitrogen-containing heterocyclic group (mono- or polycyclic); R is, inter alia, hydrogen, alkyl, heterocyclylalkyl, aryl, alkenyl, aralkyl, $-NR_2$, $-OR$, COOR, $CONR_2$ or CN; A is H or is conventionally known in the cephalosporin art; $R^2$ is H, or loweralkoxyl; p is 1 or 2; and R° is H or $CH_3$. Also disclosed are the pharmaceutically acceptable salt and ester derivatives of I; processes for the preparation of such compounds; pharmaceutical compositions comprising such compounds; and methods of treatment comprising administering such compounds and compositions when an antibiotic effect is indicated.

7 Claims, No Drawings

7-N-HETEROCYCLYL CEPHALOSPORINS AND ANTIBIOTIC PHARMACEUTICAL COMPOSITIONS CONTAINING THEM

BACKGROUND OF THE INVENTION

This invention relates to a new class of cephalosporins (I) and their pharmaceutically acceptable salts and esters which are useful as antibiotics:

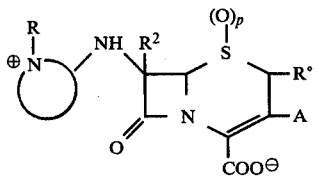

I wherein the stylized radical (hereafter referred to as R'):

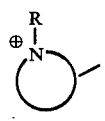

attached to the 7-amino nitrogen moiety of the cephalosporin nucleus represents a mono- or polycyclic N-containing heterocyclic group; p is 1 to 2; R° is H or CH$_3$; R is, inter alia, hydrogen, substituted and unsubstituted: alkyl, aryl, alkenyl, heterocyclylalkyl, aralkyl, —NR$_2$, COOR, CONR$_2$, —OR, or CN; R$^2$ is H, or lower alkoxyl. The heterocyclic radical R', is further defined below; also defined below is the radical "A" of structure I. However, for purposes of definition, it suffices to notice that group "A" of structure I is conventionally known in the cephalosporin antibiotic art. A is also hydrogen.

The compounds of the present invention are most conveniently isolated as the zwitterionic species demonstrated by structure I. This structure is the principal one and is utilized in the claims; however, one should be aware of other salt forms which are imposed by distinct, less preferred isolation procedures. Isolation from acidic solution provides salts which may be represented by the following structure:

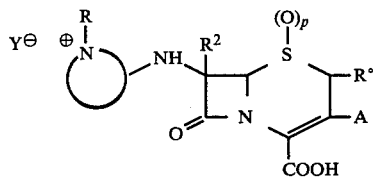

wherein Y is a pharmaceutically acceptable anion such as chloride, sulphate, acetate, propionate, citrate, tartrate or the like. Isolation from basic, solution (aqueous, for example) yields salts which may be represented by the following structures; wherein equilibrium with the imino form is indicated:

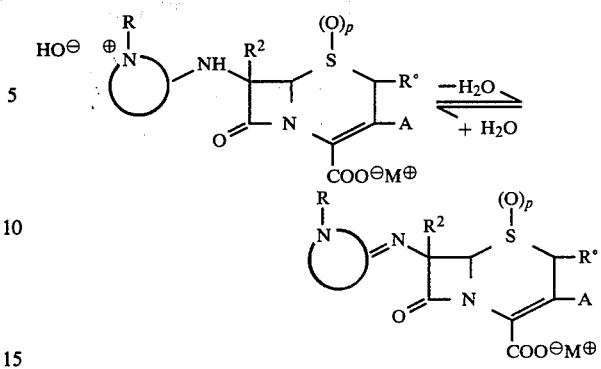

wherein M is an alkali or alkaline earth metal cation, for example, sodium, or potassium. Isolation from basic, non-aqueous solution such as dimethylformamide (DMF) in the presence of an amine NR°$_3$ (R° is, for example, loweralkyl) yields salts which may be represented by the following structure:

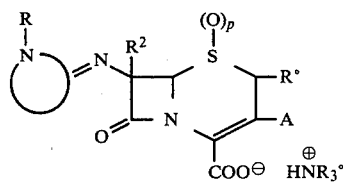

The above structure assumes that NR°$_3$ is a stronger base than the iminoheterocyclyl moiety,

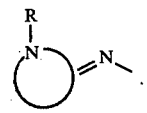

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are prepared by reacting an appropriately substituted 7-aminocephalosporin (1) with a chosen electrophilic N-heterocyclic reagent (2 or 3) calculated to provide the species of the present invention I. The following reaction diagram conveniently summarizes this process and introduces the precise identity of such electrophilic reagents and the nature of the products of this reaction (I, above).

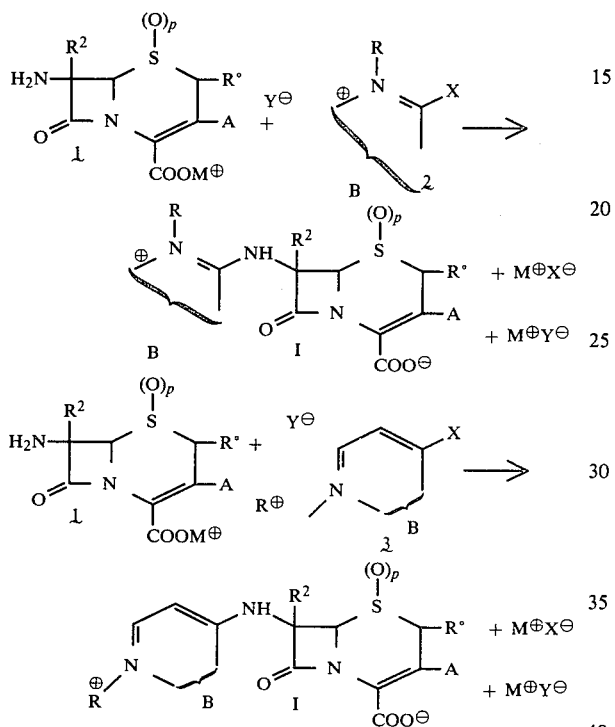

wherein:

B is, inter alia, the residue of a 5-, or a 6-membered aromatic heterocycle; or a 5,5-6,5-; or 6,6-bicyclic aromatic heterocycle; wherein the additional ring atoms are chosen either entirely as carbon, or include one or more atoms selected from S, N and O. The carbon and nitrogen atoms of any such ring may carry substituents such as substituted and unsubstituted: alkyl and alkenyl having 1-6 carbon atoms, phenyl, phenylalkyl having 1-6 carbon atoms in the alkyl moiety, 5- or 6-membered heterocyclyl wherein the hetero atom or atoms are selected from O, N or S, $-OR_2$, $-NR_2$, $-COOR$, $-CONR_2$, $-CN$, halo, $-SR$, $-SO.R_3$, $-SO_2R$, $-NHCONH_2$, $-SO_3R$, $-SO_2NR_2$ (R is defined immediately below),

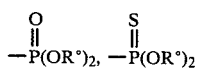

(R° is hydrogen or alkyl having 1-6 carbon atoms); wherein the substituent or substituents are selected from halogen such as chlorine or fluorine, hydroxyl, phenyl, alkyl, alkoxyl, carboxyl and phenylalkyl (each alkyl having 1-6 carbon atoms);

R is selected from H; substituted and unsubstituted: alkyl having 1-10 carbon atoms, alkenyl having 2-10 carbon atoms, phenyl, phenylalkyl, phenylalkenyl having 7-12 carbon atoms, 5- or 6-membered heterocyclylalkyl wherein the hetero atom or atoms are selected from O, N or S and the alkyl has 1-6 carbon atoms, $NR_2$, OR, COOR, CN, and $CONR_2$ (R is defined here); wherein the substituent or substituents on R are selected from halogen such as chloro and fluoro, hydroxyl, OR, $NR_2$, COOR, $CONR_2$, CN,

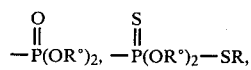

$-SO.R$, $-SO_2R$, (R° is hydrogen or alkyl having 1-6 carbon atoms), and alkyl having 1-6 carbon atoms;

R and B together may be joined to yield 6,5- and 6,6-bicyclic heterocycles in which the $N^\oplus$ is at a bridgehead;

X is a leaving group such as halogen, preferably fluorine; other leaving groups include: $OCH_3$, $SCH_3$; $OSO_2OCH_3$ $OSO_2OCF_3$,

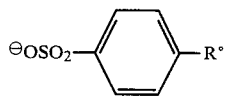

(R° is hydrogen or $C_{1-6}$ alkyl)

Y is a non-critical counter anion and representatively is: $Cl^\ominus$, $Br^\ominus$, $I^\ominus$,

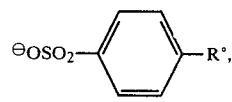

$^\ominus OSO_2OR°$, $BF_4^\ominus$, $ClO_4^\ominus$ and the like; wherein R° is H, loweralkyl or phenyl;

A is conventionally known in the antibiotic cephalosporin art; or hydrogen;

$M^\oplus$ is H, or an alkali or alkaline earth metal cation such as $Na^+$ or $K^+$, a tertiary amine salt, or the like;

$R^2$ is hydrogen or lower alkoxyl such as methoxyl

R° is H or $CH_3$; and p is 1 or 2.

In general words relative to the above reaction diagram, an appropriately substituted 7-amino cephalosporin (1) or a salt thereof in a solvent such as water at pH 7 to 8, tetrahydrofuran (THF), dimethylformamide (DMF) or the like or aqueous mixtures thereof (ideally such nonaqueous systems contain a base such as triethylamine, methyldiisopropylamine, or the like, to neutralize the acid HX produced by the addition/elimination reaction) is treated with a stoichiometric to fourfold excess of the illustrated electrophilic reagent (2 or 3) calculated to provide the desired product. Typically, the reaction is conducted at a temperature of from 0° to 40° C. and is accomplished within 1 to 5 hours. As demonstrated by the following examples, there are no undue criticalities in the parameters of reaction.

The compounds of the present invention are also prepared from starting materials wherein p=0. In such event, a final oxidation step, analogously known in the art, provides either the sulfoxide (p=1) or sulfone (p=2) embodiments of the present invention (I). In this regard, starting materials for such oxidation to provide I are disclosed and claimed in commonly assigned U.S.

patent application Ser. No. 34,035, and in concurrently filed U.S. patent application Ser. No. 62,827. These applications are incorporated herein by reference.

More specifically, relative to the above reaction scheme, a set of representative conditions may be recited to illustrate a convenient preparation of the compounds of the present invention (I); such recitation, however, is solely for purposes of demonstration and is not to be construed as introducing any undue criticalities of reaction.

Standard Reaction Conditions:

Using a pH meter coupled to an automatic burette containing 1.0 to 2.5 N aqueous sodium hydroxide, a magnetically stirred suspension of the appropriate 7-aminoceph-3-em-4-carboxylic acid in water is solubilized at pH 7 to pH 7.5 at 20° C.

The heterocyclic reagent (stoichiometric to two-fold excess) is dissolved in water at 20° C. and added to the above solution. Alkali is automatically added to maintain the selected pH in the range 7 to 7.5, the rate of addition being a measure of the extent of reaction. The reaction may also be monitored by removing aliquots at timed intervals for analysis. A particularly suitable analytical scheme is liquid chromatography, for example, high pressure liquid chromatography (HPLC) over a reverse phase column of octadecylsilane (ODS) bonded to silica, using a U.V. detector and aqueous THF (tetrahydrofuran) solution (1 to 30%) as the mobile phase.

The reaction typically takes from 15 minutes to 5 hours at 20° C. The resulting reaction solution at pH 7 is worked up by partition chromatography over a column of Amberlite XAD-2 resin, eluting with aqueous THF solutions (up to 20%) and monitoring the fractions by HPLC as above. However, with the increasing availability of large scale ODS silica columns, the preferred method of product isolation is by preparative reverse phase HPLC directly on the reaction solution at pH 7. The appropriate fractions are combined, evaporated to small volume and lyophilized to yield the product, which is conveniently characterized by I.R., U.V., NMR., and analytical HPLC.

In certain cases, the products are sufficiently insoluble in water to separate from the reaction solution at pH 7, and may be isolated simply by filtration.

Again, in reference to the above reaction diagram, the reaction when $R^2$ is alkoxyl, such as methoxyl, is sluggish. Thus a preferred preparation for species wherein $R^2$ is not hydrogen involves operating upon the product I ($R^2$=H) in the following manner to provide desired species I wherein $R^2$ is, for example, —OCH$_3$:

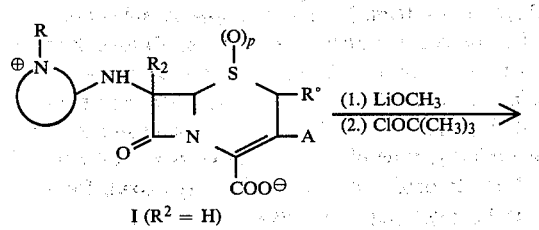

I ($R^2$ = H)

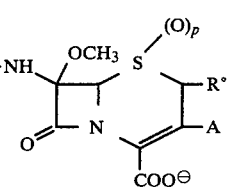

I.

An analogous reaction is known for conventional cephalosporins and penicillins; see G. A. Koppel and R. E. Koehler, J.A.C.S. 2403, 95, 1973 and J. E. Baldwin, F. J. Urban, R. D. G. Cooper and F. L. Jose, J.A.C.S., 95, 2401, 1973. According to this scheme, the starting material, in a solvent such as methanol, is treated with lithium methoxide at a temperature of −68° to 0° C.; followed by addition of the t-butylhypochlorite. The instant scheme differs from the reported procedures in that there is no need to protect the carboxyl group. It should be noted that the 3-substituent "A" may be established subsequent to the above addition/elimination reaction:

Ia

Ib wherein R', $R^2$ are as defined; and Ac is $$-\overset{O}{\underset{\|}{C}}CH_3.$$

This basic scheme, Ia→Ib, for the establishment of any desired 3-substituent A is, of course, well known in the related cephalosporin art. Representative examples are included below.

Finally, a special circumstance should be mentioned. In the basic reaction, first described, the condensation of the cephem starting material and the reagent of choice does not occur readily when the group, R, attached directly to the ring nitrogen of the reagent is hydrogen. In such circumstance, it is preferred to employ a quaternized ring nitrogen prior to reaction. The quaternizing group may be removed after the amino heterocycle bond has been formed to yield species of the present invention, I, wherein R is hydrogen:

Ic

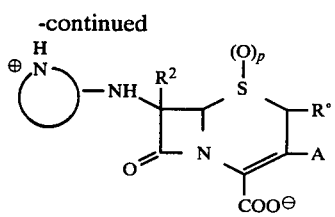

wherein R is —CH$_2$OCH$_3$, —CH$_2$OCOCH$_3$ or the like. According to the above scheme, Ic→Id, the group R is conveniently removed by treating Ic in anhydrous sulpholane at 20° C. with a 3- to 4-fold molar ration of I Si(CH$_3$)$_3$, followed by hydrolysis to yield Id. A representative example is included below. The reaction may schematically be shown as follows:

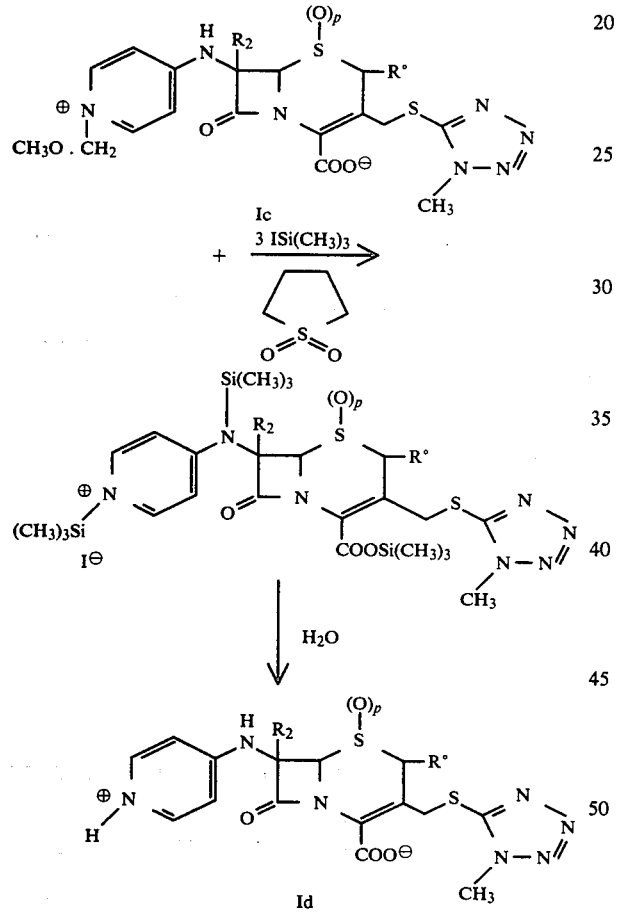

The product Id is then isolated directly from the reaction solution at pH 7 by preparative reverse phase HPLC as already described.

IDENTIFICATION OF REAGENTS

The necessary electrophilic, N-heterocyclic reagents 2 and 3 are known and commercially available or may be prepared according to known procedures; see, for example: *Advances in Heterocyclic Chemistry*, pp. 1–56, Vol. 3 (1964) and pp. 71–121, Vol. 22 (1978); Academic Press. The following list representatively illustrates such reagents.

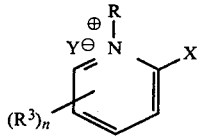
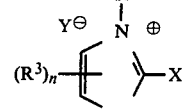

wherein all symbols have previously been defined; the dotted line indicates both saturated and unsaturated rings. Relative to the above-listed reagents, the preferred values for the radical R which is directly attached to the ring nitrogen atom are: hydrogen; lower-alkyl having from 1–10 carbon atoms; substituted alkyl wherein the substituent is chloro, fluoro, hydroxyl, carboxyl, amino, sulfo, and mono- and dialkylamino wherein each alkyl has 1–6 carbon atoms; phenylalkyl (alkyl moiety having 1–6 carbon atoms) and substituted phenylalkyl wherein the substituents are selected from chloro, fluoro, carboxyl, amino, hydroxyl, lower alkoxyl having from 1–6 carbon atoms, sulfo,

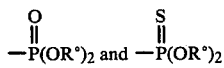

(R° is hydrogen or alkyl having 1–6 carbon atoms). The quinolizinium and indolizinium examples are a special category of preferred values of R, in that R is there an integral part of a bicyclic system (R', defined above).

The preferred values for the other, non-position-specific ring substituent R³ are: chloro, fluoro, carboxyl and loweralkyl having from 1–6 carbon atoms; substituted lower alkyl wherein the substituent is carboxyl, cyano, alkoxyl having 1–6 carbon atoms, phenyl, and phenyloxy; the preferred value for n is 0 or 1. The preferred leaving group X is chloro or fluoro.

Identification of A

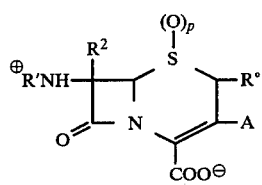

The group A, when other than hydrogen, in structure I embraces all known 3-substituents in the cephalosporin art. The following references are incorporated herein by reference to the extent that they recite preferred values of A in structure I: U.S. Pat. No. 4,138,486 (6 Feb. 1976); and British Pat. No. 1455016 (10 Nov. 1976). Especially preferred values for A include:

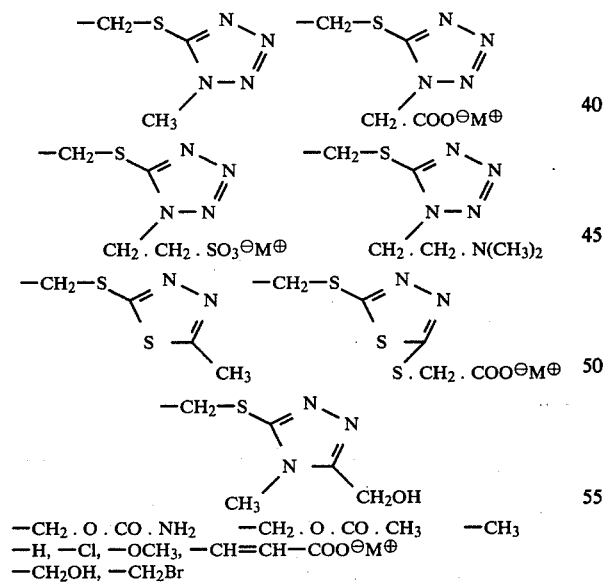

(Y is as previously defined and may be, inter alia, acetate; M⊕ is a pharmaceutically acceptable cation such as Na⊕, K⊕ or the like.)

Typical compounds of Formula I, above, are compounds wherein:

A is selected from the group consisting of: hydrogen,

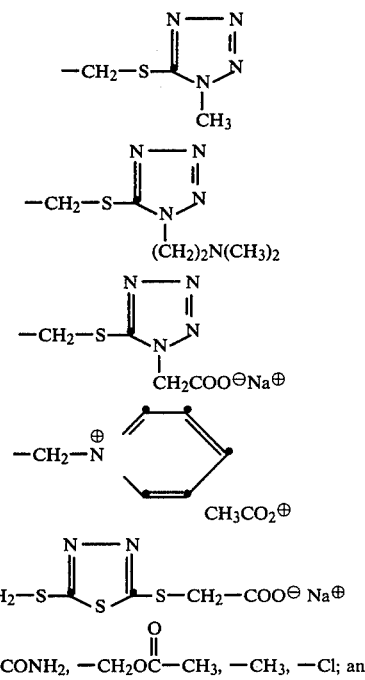

R' is selected from:

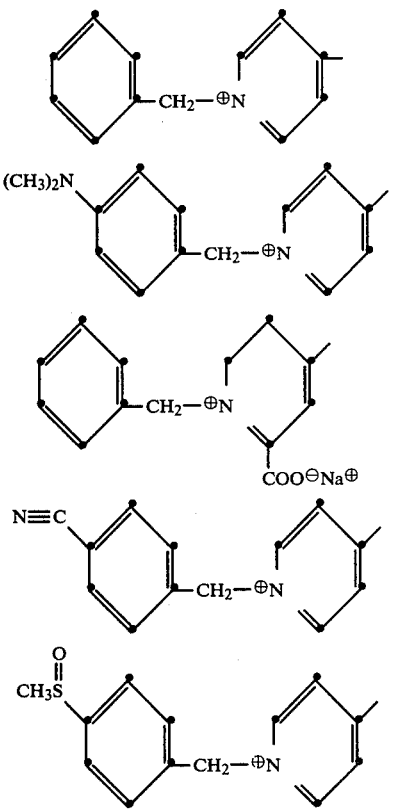

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia coli, Klebsiella pneumoniae, Bacillus subtilis, Salmonella typhosa,* Psuedomonas and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure zwitterionic compound in sterile water solution or in the form of a soluble powder intended for solution. The pH of such solutions typically will correspond to the zwitterionic point; however, consideration of individual properties of solubility and stability may require such aqueous solutions to have a pH other than that of the zwitterionic point, for example in the range of 5.5 to 8.2

The following examples, illustrate but do not limit the product, process, compositional or method of treatment aspects of the present invention. All reaction temperatures are in °C.

EXAMPLE 1

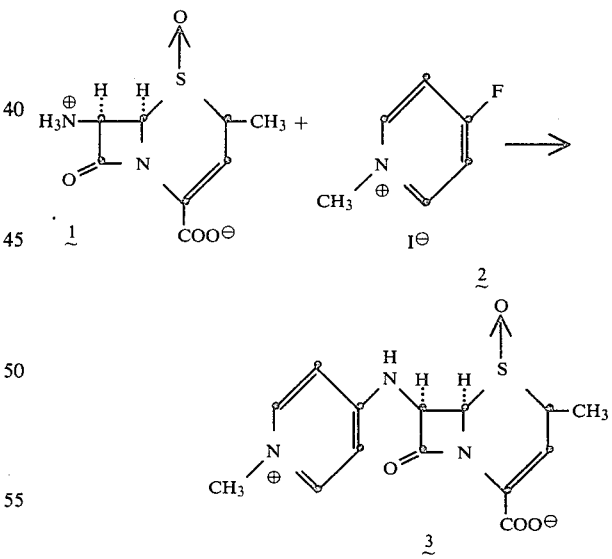

With an end-point set at pH=7.5, aqueous 1.0 N-NaOH is added from an automatic burette to a vigorously magnetically stirred suspension of 1 (0.73 mmole), in distilled, deionized water (3.0 ml) at 20° C.

The reagent 2,4-fluoro-1-methylpyridinium iodide is added (261 mg, 1.10 mmole) in one portion to the above stirred solution; it dissolves instantly, causing a rather slow response from the automatic burette to maintain pH 7.5 Cessation of base from the automatic burette signals completion of the reaction 1+2→3.

The resulting reaction solution is put on a 3.6×46 cm column of Amberlite XAD-2 resin prepared in distilled, deionized water; eluting with the same solvent, water. With the flow rate set at 1 drop/sec., individual fractions comprising 200 drops each are collected. Absorbance at 254 nm is observed. Unreacted starting materials 1 and 2 come off first, their departure being signaled by a long minimum in absorbance at 254 nm. The eluting solvent is then changed to aqueous 5% tetrahydrofuran (THF). Fractions containing the product 3 are pooled and lyophylized to yield pure product 3. The pooled fractions are shown to contain pure 3 on assay by HPLC, using a $C_{18}$ reverse phase column and aqueous 10% THF as the mobile phase.

EXAMPLE 2

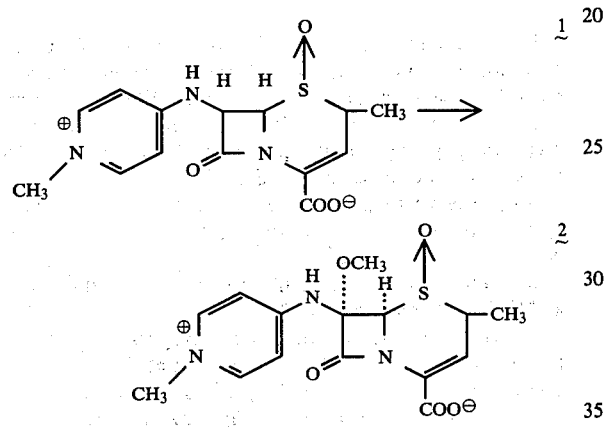

The product of Example 1 (1, above, 168 mg., 1.0 mol) is dissolved in anhydrous methanol (1.0 ml) at r.t. (20° C.) and the solution is cooled to −68° C. under an atmosphere of dry $N_2$, in an acetone/solid $CO_2$ bath. A solution of lithium methoxide in methanol (1.83 ml, 5.0 mol., of 1.5N-LiOMe/MeOH) is added by syringe through a rubber septum to the magnetically stirred solution. After 2 minutes t-butylhypochlorite (t-BuOCl, 79 μl, density=0.91, 1.2 mol.) is added by syringe, as above. Stirring is continued for 5 minutes at −68° C.; whereupon the reaction is quenched by adding acetic acid (315 μl 10.0 mol). The solution is evaporated at 25° C. under reduced pressure and redissolved in water (20 ml) and then lyophilized.

The resulting product is chromatographed in pure distilled water over a 3.1×43 cm. column of Amberlite XAD-2 resin. Initial elution was by water at a flow rate of 2 drops/sec.; individual fractions comprising 400 drops each (∼26 ml) are collected. Absorbance at 254 nm is observed. On the shoulder of increasing absorbance, the solvent is changed to aqueous 5% THF. Fractions comprising the product are pooled and lyophylized to yield crude 2 which is purified by preparative reverse phase liquid chromatography to yield the desired product 2.

Following the procedure of Examples 1 and 2, the following species are obtained when the corresponding desmethyl starting material is employed:

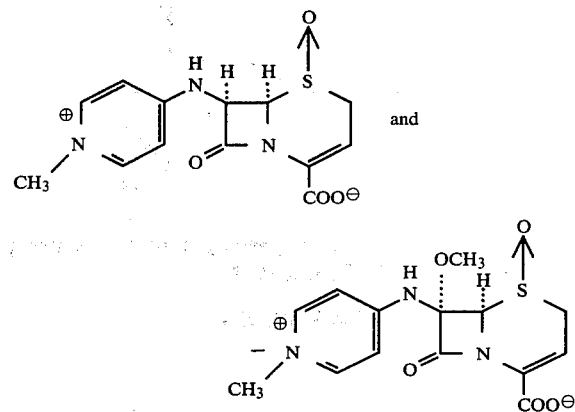

EXAMPLE 3

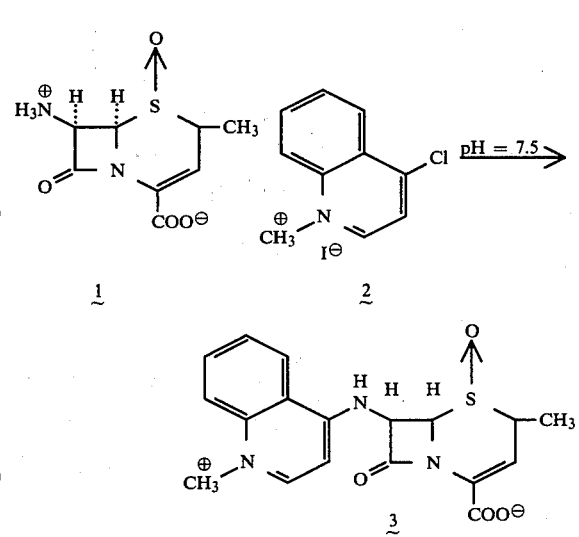

With the end point set at pH=7.5, aqueous NaOH (2.5 N) is added from an automatic burette to a magnetically stirred suspension of (1) (1.836 mmole). The reagent 2,4-chloro-1-methylquinolinium iodide (0.673 g; 2.203 mmole), is added in one portion to the above solution. Progress of the reaction is monitored by analytical liquid chromatography, using a $C_{18}$ reverse phase column, aq. 10% THF as the mobile phase, and a UV detector. More 4-chloro-1-methylquinolinium iodide (2) (168 mg, 0.55 mmole) is added, and stirring at 20°0 C./pH 7.5 continued for a total of 3 hours. Thereafter, the solution is diluted to 40 ml with distilled water and worked up directly by preparative reverse phase liquid chromatography using a 5×30 cm $C_{18}$ column, aq. 2.5%/THF as the mobile phase and a variable wave length UV detector. The fractions comprising 3 are evaporated at 35° C./0.1 mm to 100 ml then lyophylized yielding 3.

The corresponding desmethyl species

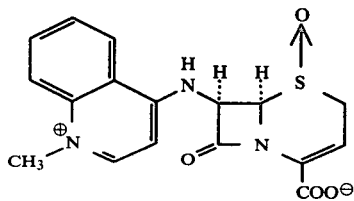

is obtained when the corresponding desmethyl starting material replaces 1 of Example 3.

EXAMPLE 4

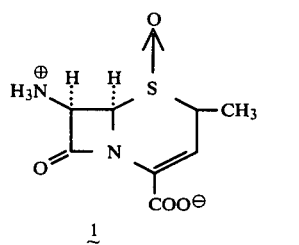

1

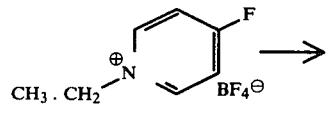

2

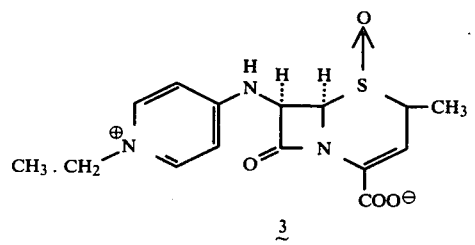

3

With the end-point set at pH 7.5, aqueous NaOH (1.0 N) is added from an automatic burette to a magnetically stirred suspension of 1 (0.609 mmole) in distilled deionized water (2.5 ml) at 20° C. The reagent 4-fluoro-1-ethylpyridinium tetrafluoroborate,2,(378 mg, 70% purity, 1.22 mmole) is dissolved in distilled deionized water (0.5 ml) and added in one portion to the above solution at 20° C. After 1 hour, the reaction solution is extracted with CH₂Cl₂ (2×20 ml) and ether (20 ml) to remove contaminants. The polar, zwitterionic product is then isolated from the pH 7.5 aqueous phase by reverse phase liquid chromatography.

EXAMPLE 5

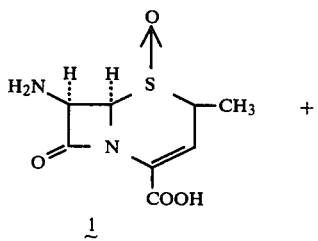

1

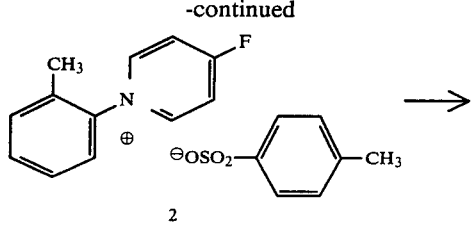

2

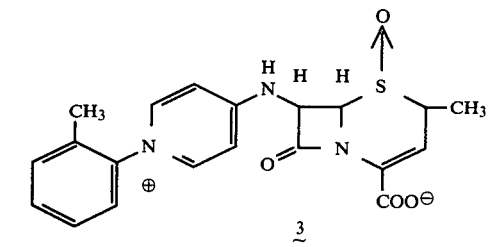

3

With the end-point set at pH 7.0 aqueous NaOH (2.5 N) is added from an automatic burette to a magnetically stirred suspension of 1 (0.5 g) in distilled deionized water (4.0 ml) at 20° C. The reagent 4-fluoro-1-(2'-methylphenyl)-pyridinium p-toluenesulphonate,2, (0.84 g) is dissolved in distilled, deionized water (2.0 ml) giving a clear pale pink solution which is added rapidly (½ min) to the above sodium cephalosporate solution with magnetic stirring at 20° C.

In 2 hours the mixture is filtered and the solid is dried at 25° C./0.1 min. to yield 3.

Purification is accomplished by preparative reverse phase L.C. using a 2.0×61 cm. Bondapak C₁₈ (37–75μ) column, a U.V. detector and aq. 5% THF as the mobile phase at a flow rate of 19.8 ml/minute. The maximum loading of the column under the above conditions is 120 mg. The combined eluates from repetitive injections are evaporated to 150 ml and lyophilized to yield 3. By subjecting the filtrate from crude 3. to preparative reverse phase L.C. as above, an additional quantitiy of pure 3. is obtained.

EXAMPLE 6

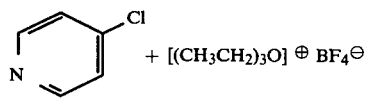

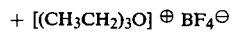

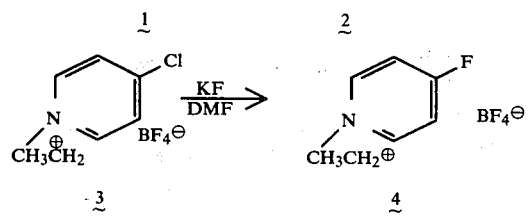

To a solution of 4-chloropyridine (5.90 g, 1.0 mmole; 1) in nitromethane (10 ml) cooled to 0° C. in an ice bath, is added rapidly (over 3 minutes) a solution of triethyloxonium tetrafluoroborate (2; 9.87 g) in nitromethane (20 ml) forming an intensely orange solution. After 10 minutes at room temperature, 20° C., the solution is evaporated at 60° C./1.0 mm leaving a partially crystalline orange gum. Acetonitrile (10 ml) is added and the solution heated to 60° C. The solution becomes pale yellow and shows some very finely divided material in suspension.

This mixture is left at 20° C. overnight with no change in appearance. It is then filtered, the solid washed with CH3CN, and discarded. Evaporation of the filtrate leaves a viscous oil which slowly crystallized at ~60°/0.5 mm. Acetonitrile (10 ml) is added and the solution heated at 60° C. for 5 minutes, cooled to 20° C., some insolubles filtered off and the solution evaporated at 60°/0.5 mm, leaving an off-white slightly oily solid (10.16 g 64%), m.p. wide range 70°–98°, shown by NMR to be the correct product: 4-chloro-1-ethylpyridinium tetrafluoroborate (3) NMR - T60 (D$_2$O) 1.63 (t, J=7.5 Hz, 3H, —CH$_3$); 4.63 (q, J=7.5 Hz, 2H, N$^\oplus$—CH$_2$—); 8.14 (d, J=7 Hz, 2H, H$_3$+H$_5$); 8.83 (d, J=7 Hz, 2H, H$_2$+H$_6$). A portion, (10.0 g, 1.0 mol) of 3, 4-chloro-1-ethylpyridinium tetrafluoroborate, is dissolved in sieve-dried DMF (30 ml) and commercial anhydrous KF (8.86 g 3.5 mol.) added, producing a yellow brown mixture. The solution/suspension is stirred at 20° C. under N$_2$ over the weekend, remaining a suspension and becoming dark brown.

Ether is added (100 ml) to the above mixture, precipitating a dark brown oily solid which is separated by decanting the clear orange supernatant layer. The insoluble product is washed with more ether (2×25 ml) and is then extracted with nitromethane (3×20 ml) with filtration to remove the inorganic salts. The combined CH$_3$NO$_2$ filtrates are combined and evaporated at 50° C./1 mm. leaving a dark brown viscous oil (6.062 g) shown by NMR to be a mixture of the desired 1-ethyl-4-fluoropyridinium tetrafluoroborate 4 (70%) NMR [A] and 1-ethyl-4-pyridene. NMR [B] NMR T60 (D$_2$O) NMR [A] N$^\oplus$CH$_2$ 4.68 (q.); H$_3$+H$_5$ 7.94 (m); H$_2$+H$_6$ 8.96 (m) NMR [B] N—CH$_2$ 4.22 (q); H$_3$+H$_5$ 6.86 (d); H$_2$+H$_6$ 8.10 (d) J=7 Hz).

EXAMPLE 7

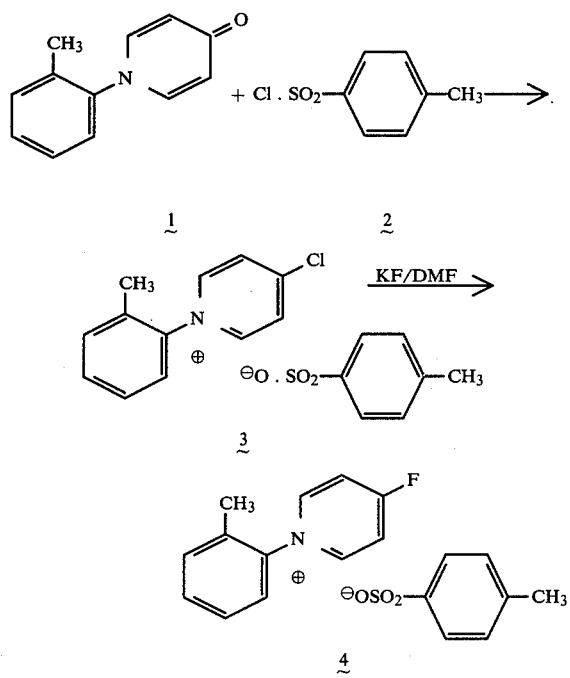

1-(o-tolyl)-4-pyridone (1; 1.0 g) is dissolved on heating in toluene (10 ml) and the solution is dried by boiling out the azeotrope. To the solution at gentle reflux is added recrystallized p-toluenesulphonyl chloride (2; 1.03 g) in one portion. The solid dissolves immediately, forming an opaque white suspension, which in a few more seconds changes to a pale brown oil precipitated from a clear solution. After a total of 5 minutes at reflux, the mixture is cooled to 20° C.; the supernatant toluene decanted, the oil washed with more toluene (5 ml) with decantation, then heated at 50° C./0.1 mm to remove the last traces of toluene, becoming a glass on cooling (3; 2.054 g) NMR: (T-60, D-DMSO): 2.18 (s, 3H, tolyl-CH$_3$); 2.31 (s, 3H, tosyl-CH$_3$); 7–7.7 (aromatic) 8.58 (d, 2H, J=7.0 Hz, H$_3$+H$_5$ py.); 9.30 (d, 2H, J=7.0 Hz, H$_2$+H$_6$ py.)

Commercial anhydrous KF (1.255 g, 4.0 mol) is added to the above product 3 (2.054 g, 1.0 mol) followed by sieve-dried dimethylformamide (DMF) (5.0 ml.). The mixture is magnetically stirred at room temperature 20° C. under N$_2$ becoming a pale pink suspension of KF in the DMF as the chloropyridinium tosylate slowly dissolves. After 45 minutes, the mixture, unchanged in appearance is filtered; solids are washed with dry DMF (2×0.5 ml) and the combined pinkish brown filtrate is evaporated at 50° C./0.1 mm. leaving a pale brown gum, which is extracted with hot (70°) toluene (3×10 ml; previously azeotroped dry) with decantation. Some flocculent white solid (probably KF) is decanted off with the toluene and is filtered off. The combined toluene extracts are evaporated at 50° C./0.1 mm leaving a colorless crystalline solid (141 mg) which is shown by NMR (T60; D-DMSO) to be starting material 1, 1-(o-tolyl)-4-pyridone.

Material insoluble in the hot toluene is a pale brown syrup which gradually solidifies at 50° C./0.1 mm to a pale pink mass, which is broken up and left at 20° C./0.1 mm overnight to remove all traces of solvents.

The resulting product 4 is finally obtained as a pale pink powder (1.596 g). NMR-T60 (D-DMSO) 8.39 (dd, 2H, J$_{(3,5)(2,6)}$=7.0 Hz, J$_{(3,5)F}$=7.0 Hz) 9.41 (dd, 2H, J$_{(3,5)(2,6)}$=7.0 Hz J$_{(2,6)F}$=5.0 Hz NMR-T60; (D$_2$O) 8.04 (dd, H$_3$H$_5$); 9.02 (dd, H$_2$H$_6$).

EXAMPLE 8

Preparation of

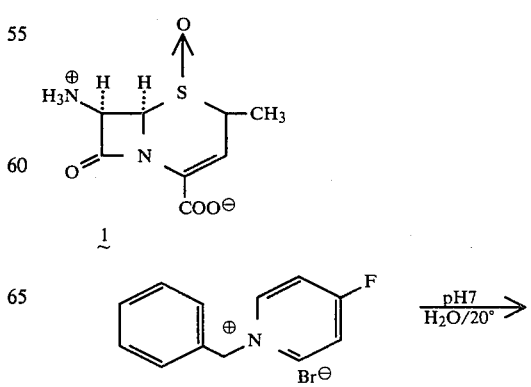

-continued

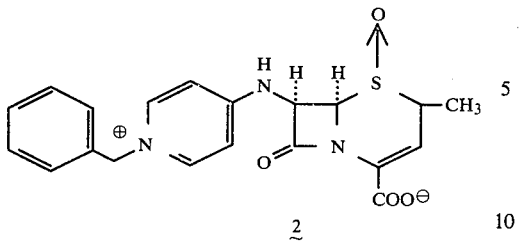

One gram of 1 is suspended in 10 ml. water and dissolved by addition of 1N NaOH from an automatic burette set at pH of 7. 1-benzyl-4-fluoro-pyridinium bromide, 1.50 grams in 5 ml. of water is added. The pH is maintained at 7. After 2.5 hours the reaction is filtered. The product is isolated directly from the filtrate by preparative reverse phase liquid chromatography using a 5×30 cm $C_{18}$ column, aq. 1.5% THF as the mobile phase, and a variable wavelength U.V. detector. The fractions comprising 2 are evaporated at 35°/0.1 min. to 150 ml. then lyophylized to yield 2.

EXAMPLE 9

Preparation of:

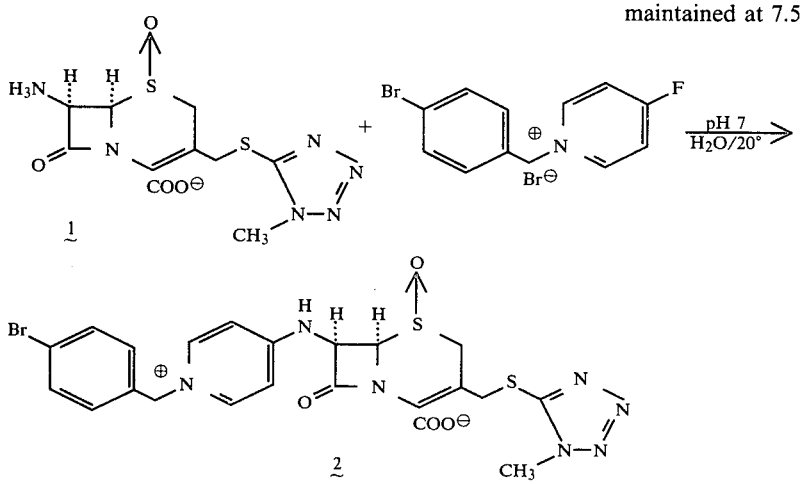

One gram of 1 is suspended in water (10 ml) and dissolved by the addition of 1N NaOH from an automatic burette set at a pH of 7.5. The mixture is filtered and the filtrate is added to 2.9 mmoles of 1-(4'-bromobenzyl)-4-fluoro-pyridinium bromide. The pH is maintained at 7.5 with 1N NaOH. The precipitate is isolated, after 1.0 hour, by filtration and dried. This solid is extensively washed with 100 ml. of methanol to extract the desired product. This methanol solution is concentrated under reduced pressure to a solid which is triturated with water and then acetone. The remaining solid is dissolved in 30% tetrahydrofuran and water, and chromatographed on $\mu C_8$ Chromegaprep reverse phase column in 30% THF/water. The eluted fractions are concentrated under reduced pressure and lyophilized to yield the desired product, 2.

EXAMPLE 10

Preparation of

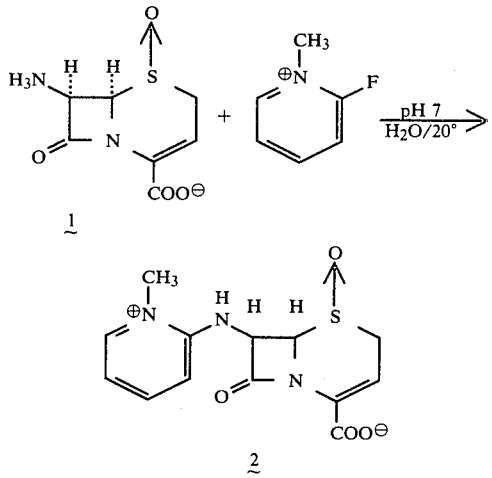

One gram of 1 is suspended in 6 ml. water and dissolved by the addition of 1N NaOH from an automatic burette set at a pH of 7.5. 2-Fluoro-1-methyl-pyridinium iodide, 1.34 grams in 2 ml. of water is added. The pH is maintained at 7.5 with 1N NaOH. After five hours the reaction is diluted with water and washed with five equal portions of ethylacetate. The aqueous phase is filtered and concentrated under reduced pressure to remove remaining EtOAc. The resulting solution is chromatographed on a Waters Prep 500 $C_{18}$ reverse phase column eluting with aqueous 1.25% tetrahydrofuran and monitoring fractions with a variable wavelength U.V. detector. The main fraction is concentrated and lyophylized yielding 2.

EXAMPLE 11

Preparation of

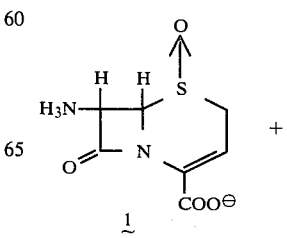

-continued

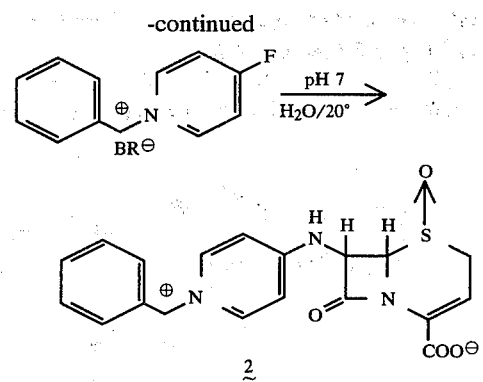

One gram 1 is suspended in H₂O (10 ml) and dissolved by the addition of 1N NaOH from an automatic burette set at a pH of 7.5. 1-Benzyl-4-fluoropyridinium bromide, 1.61 grams, is dissolved in water (4 ml.) and added to the above solution. The pH is maintained at 7.5 with 1N NaOH. After two hours at 25°, the solution is chromatographed in a Waters Prep. 500 C₁₈ reverse phase column, eluting with aqueous 1.5% aqueous tetrahydrofuran and monitoring fractions with a variable wavelength U.V. detector. The main fraction is evaporated to 150 ml at 35°/0.1 min., then lyophylized yielding 2.

EXAMPLE 12

Preparation of

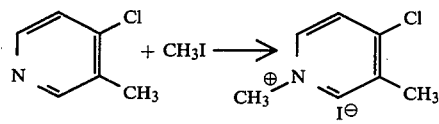

4-Chloro-1,3-dimethyl-pyridinium Iodide

A solution of 7.2 g. (56.6 mmoles; 6.25 ml.) of 4-chloro-3-methyl pyridine in 39.4 g. (283 mmoles; 17.3 ml.) of cold methyl iodide is kept at 5° for 20 hours. The mixture is diluted with 30 ml. of ether and filtered. The solid is washed with ether and dried yielding 11.2 g. of 4-chloro-1,3-dimethyl-pyridinium iodide.

NMR (60 MHz-DMSO-d₆) 2.5 (s, 3H), 4.3 (s, 3H), 8.3 (d, 1H), 8.9 (dd, 1H), 9.1 (d, 1H).

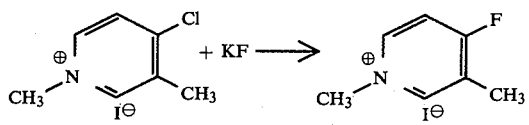

4-Fluoro-1,3-dimethyl-pyridinium Iodide

A solution of 5.4 g. (20 mmoles) of 4-chloro-1,3-dimethyl-pyridinium iodide in 30 ml. of dimethylformamide is treated with 4.1 g. (70 mmoles) of anhydrous KI and stirred at 55° for 24 hours. Stirring is continued at 25° for 48 hours. The mixture is filtered and the filtrate is diluted with an equal volume of ether. The solid which separates is filtered, washed with ether and dried to yield 3.57 g. of 4-fluoro-1,3-dimethyl pyridinium iodide. NMR (60 MHz. DMSO-d₆) 2.2 (s, 3H), 4.3 (s, 3H), 8.1 (t, 1H), 9.1 (m, 2H).

EXAMPLE 13

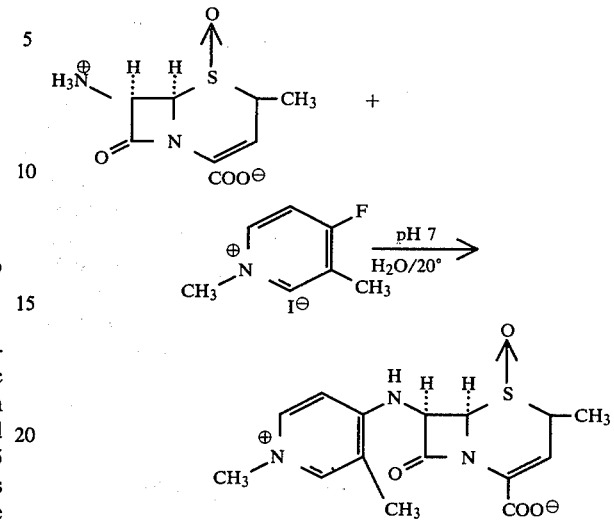

A mixture of 1 g. of 2-carboxy-4-methyl-7β-amino-8-oxo-5-thia-1-azabicyclo[4.3.0]oct-2-ene in 10 ml. of H₂O is neutralized to pH 7.4 with 1N NaOH in a pH-Stat. and 1.77 g (1.5 equivalents) of 4-fluoro-1,3-dimethylpyridinium iodide is then added. The reaction solution, after 6 hours, is diluted to 100 ml. with water and freeze-dried yielding crude product. The crude is purified by high performance liquid chromatography using a Waters Prep. 500 C₁₈ reverse phase column and the fraction containing the product (identified by a U.V. maximum at 282 nm) is concentrated. The concentrate is freeze-dried to give pure product.

EXAMPLE 14

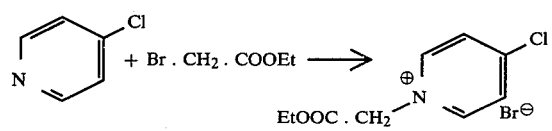

1-Carboethoxymethyl-4-chloropyridinium bromide

A solution of 1.1 g. (10 mmoles; 0.95 ml.) of 4-chloropyridine in 10 g. (60 mmoles) of ethyl bromoacetate is kept at 5° for 48 hours. The mixture is diluted with 15 ml. of ether, filtered and the solid is washed well with ether.

After drying 2.29 g. of 4-chloro-1-carboethoxymethyl pyridinium bromide is obtained.

NMR (60 MHz - DMSO - d₆) 1.3 (t, 3H), 4.3 (q, 2H), 5.9 (s, 2H), 8.6 (d, 2H), 9.3 (d, 2H).

EXAMPLE 15

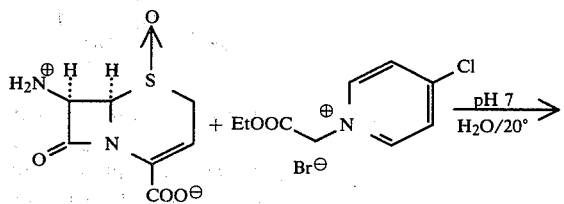

-continued

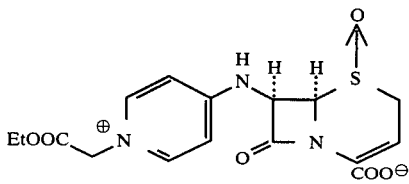

A mixture of 1 g. of 2-carboxy-7β-amino-8-oxo-5-thia-1-azabicyclo[4.2.0]oct-2-ene in 10 ml. of H₂O is stirred and neutralized to pH 7.4 with 1N NaOH in a pH-Stat. A 1.55 g (1.0 equivalent) sample of 4-chloro-1-carboethoxymethylpyridinium bromide is added and titration continued with 1N NaOH to pH 7.0. Cessation of base addition signals completion of reaction.

The reaction solution is washed with three 10-ml. portions of ethyl acetate, diluted to 50 ml. with water and freeze-dried to yield crude product.

A 500-mg. portion of the crude product in 10 ml. of water is centrifuged. The supernatant is purified by high performance liquid chromatography. Fractions containing product are concentrated and freeze-dried to yield pure product.

EXAMPLE 16

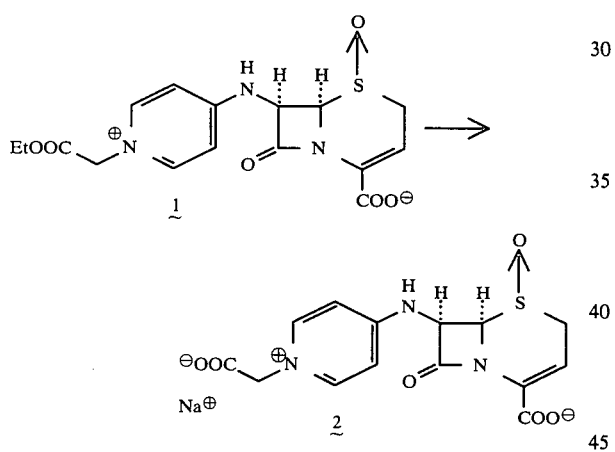

A solution of 25 mg. of 1 in 2 ml. of H₂O is titrated in a pH-stat with 0.05N NaOH to pH 9. On consumption of the theoretical quantity of aq. 0.05N NaOH (ca. 1.0 hour), the pH of the reaction solution is adjusted to 7 and freeze-dried to yield 2.

EXAMPLE 17

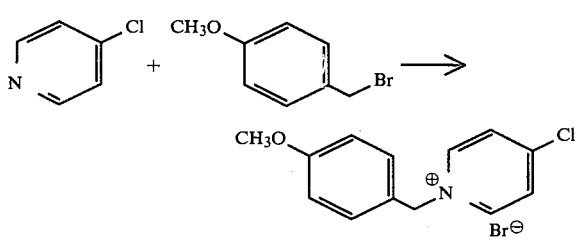

A cold solution of 200 mmoles of 4-methoxybenzyl bromide in 100 ml. of benzene is treated with 5 g. (50 mmoles; 4.6 ml.) of 4-chloropyridine and kept at 5° for 48 hours. The precipitate is filtered, washed well with ether and dried to give 7.2 g. of 1-(4-methoxybenzyl)-4-chloropyridinium chloride.

NMR (60 MH$_z$ - DMSO-d$_6$) 3.7 (s, 3H), 5.8 (s, 2H), 6.9 (d, 2H), 7.5 (d, 2H), 8.3 (d, 2H), 9.2 (d, 2H).

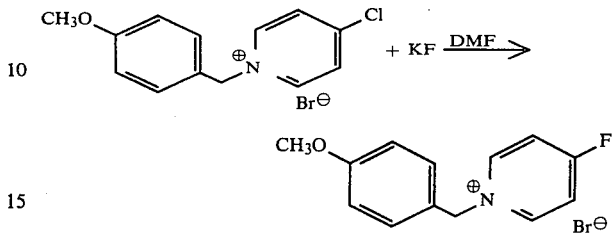

A mixture of 1.25 g. (4 mmoles) of 1-(4-methoxy-benzyl)-4-chloropyridinium bromide and 0.93 g. (15 mmoles) of anhydrous KF in 10 ml. of dry dimethylformamide was stirred at 25° under N₂. After 2.5 hours the mixture was filtered and the filtrate was concentrated to a residual 2.2 g. of oily 1-(4-methoxybenzyl)-4-fluoro-pyridinium bromide.

NMR (60 MH$_z$ - D₂O) 3.9 (s, 3H), 5.9 (s, 2H), 7.15 (d, 2H), 7.7 (d, 2H), 8.1 (t, 2H), 9.1 (q, 2H).

EXAMPLE 18

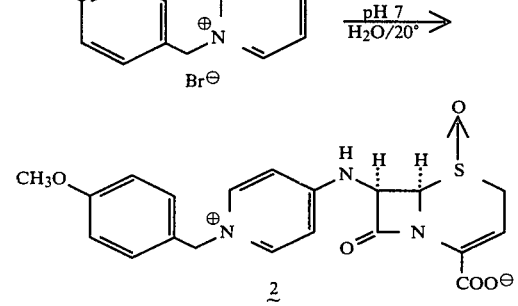

A mixture of 1.35 g. of 2-carboxy-7β-amino-8-oxo-5-thia-1-azabicyclo [4.2.0]oct-2-ene in 8 ml. of H₂O is stirred and titrated with 2.5N NaOH in a pH-stat to pH 7.5. To this solution is added a solution of 1.49 g. (1.0 equivalent of 1-(4-methoxybenzyl-4-fluoropyridinium bromide in 5 ml. of water and titration at pH 7 is continued. After cessation of base, the reaction is complete and the product is isolated from the solution by chromatography on a Waters Prep. 500 C₁₈ reverse phase column, using aqueous 1.5% THF as the mobile phase and monitoring the eluate with a variable wavelength U.V. detector. The main fraction is evaporated at 35°/0.1 min. to 150 ml. and lyophylized to yield 2.

EXAMPLE 19

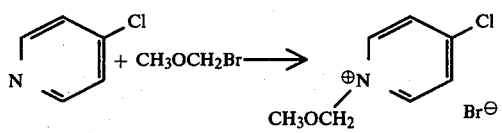

A solution of 5 g. (40 mmoles; 3.35 ml.) of bromomethyl methyl ether in 20 ml. of ether is cooled to −10° and treated dropwise over 20 minutes while being stirred with a solution of 2 g. (20 mmoles; 1.9 ml.) of 4-chloropyridine in 8 ml. of ether. An immediate precipitation of a white solid occurs. Stirring is continued an additional 20 minutes and the solid is filtered and washed with ether and dried to yield 3.8 g. of 1-methoxymethyl-4-chloropyridine.

NMR (60 MH$_z$ - D$_2$O) 2.5 (s, 3H), 4.85 (s, 2H), 7.3 (d, 2H), 8.0 (d, 2H).

EXAMPLE 20

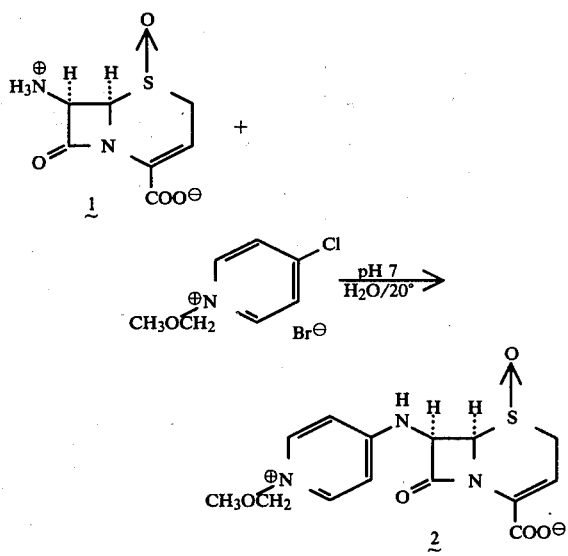

A mixture of 340 mg. of 1 in 5 ml. of water is neutralized to pH 7.0 with 1 N NaOH in a pH-stat. The solution is treated with 507 mg. of 1-methoxymethyl-4-chloropyridinium bromide and titration with 1 N NaOH is continued. After cessation of base addition, the reaction is complete and is diluted to 25 ml. with water and freeze-dried to give crude product, which is purified by HPLC on a 2.0×61 cm. Bondapak C$_{18}$ column in the system 1.5% tetrahydrofuran in water. The combined product fractions are concentrated and the concentrate is freeze-dried to give pure 2.

EXAMPLE 21

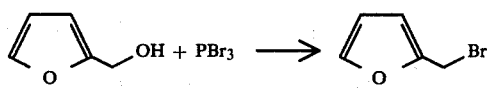

1-Furfuryl-4-chloropyridinium Bromide

A solution of 4 g. (40 mmoles; 3.5 ml.) of furfuryl alcohol in 40 ml. of ether is cooled to 5°, stirred and treated dropwise with a solution of 4 g. (14.8 mmoles;

1.4 ml.) of PBr$_3$ in 6 ml. of ether over a period of 30 minutes. After an additional 15 minutes the ether solution is decanted from a dark insoluble oil and stirred for 15 minutes at 5° with one gram of K$_2$CO$_3$ (anhydrous). The mixture is filtered and the filtrate is treated with 2 g. (20 mmoles; 1.9 ml.) of 4-chloropyridine. The precipitate which forms immediately is filtered and the filtrate is treated with an additional 2 g. (20 mmoles; 1.9 ml.) of 4-chloropyridine and is kept at 25° for 5 days. The solid which separates is filtered and washed well with ether and dried to give 1.7 g. of 1-furfuryl-4-chloropyridinium bromide.

NMR (60 MH$_z$ - D$_2$O) 5.9 (s, 2H), 6.6 (q, 1H), 6.95 (d, 1H), 7.7 (d, 1H), 8.25 (d, 2H), 8.95 (d, 2H).

EXAMPLE 22

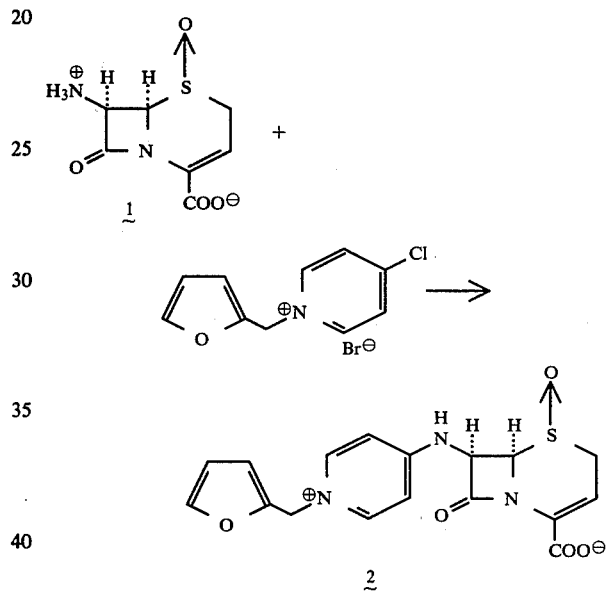

A mixture of 340 mg. of 1 in 5 ml. of water is neutralized to pH 7.0 with 1 N NaOH in a pH-stat. To this solution is added 1-furfuryl-4-chloropyridinium chloride (546 mg), and titration is continued with 1 N NaOH. After cessation of base addition, the reaction solution is diluted to 50 ml. with water and freeze-dried to give crude product, which is purified by HPLC on a 2.0×61 cm Bondapak C$_{18}$ reverse phase column in the system 2.5% tetrahydrofuran in water, using a U.V. detector. The fractions containing product are combined and concentrated and the concentrate is freeze-dried yielding pure 2.

EXAMPLE 23

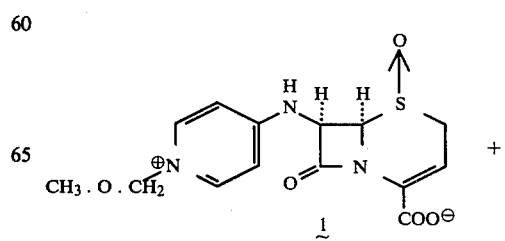

-continued

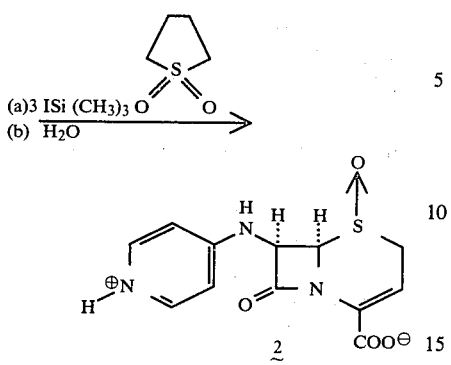

Iodotrimethylsilane (3.0 mmoles) is added by syringe through a rubber septum to a soltution of 1 (1.0 mmole) in dry tetramethylenesulphone (5 ml) at 20° C. in an atmosphere of dry nitrogen. The mixture is magnetically stirred at 20° C. for 24 hours and is then diluted with an equal volume of water. The product is isolated directly from this solution by preparative high performance liquid chromatography over a 5×30 cm $C_{18}$ Bondapak reverse phase column with aqueous 2% tetrahydrofuran as the mobile phase and monitoring the eluate with a variable wavelength U.V. detector. The appropriate eluate fraction is evaporated at 25°/1 mm to approximately 100 ml. then lyophylized to yield 2.

EXAMPLE 24

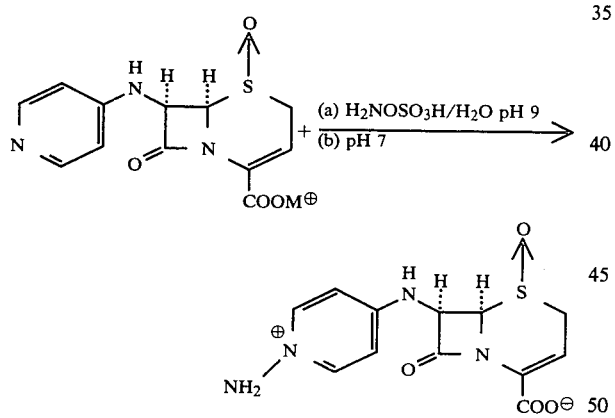

The product of Example 23 (2 mmole) is dissolved in water (20 ml) and the pH of the solution adjusted to 9 by adding aq. 2.5 N NaOH from an automatic burette controlled by a pH stat. The solution is cooled to 2° in an ice bath and hydroxylamine O-sulphonic acid (4 mmole) added with magnetic stirring. The mixture is stirred at 20°/pH=9 for 10 hours. The pH is then adjusted to 7 by adding aq. 2.5 N-HCl and the product is isolated directly from this solution by preparative reverse phase HPLC over a 5×30 cm $C_{18}$ Bondapak column with aq. 2% tetrahydrofuran as the mobile phase and monitoring the eluate with a variable wavelength detector. The appropriate eluate fraction is evaporated at 25°/1 mm to approximately 100 ml then lyophylized to yield the desired product characterized by U.V., IR, and NMR.

EXAMPLE 25

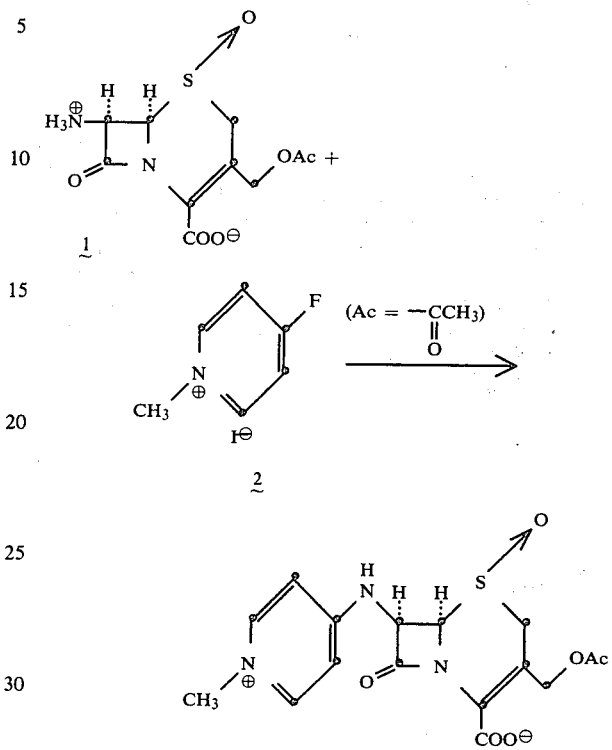

With an end-point set at pH=7.5, aqueous 1.0 N-NaOH is added from an automatic burette to a vigorously magnetically stirred suspension of 1 (0.73 mmole, is distilled, deionized water (3.0 ml) at 20° C.

The reagent 2, 4-fluoro-1-methylpyridinium iodide is added (261 mg, 1.10 mmole) in one portion to the above stirred solution; it dissolves instantly, causing a rather slow response from the automatic burette to maintain pH 7.5. The addition of base from the automatic burette practially ceased after 2.0 hours, thus signaling completion of the reaction 1+2→3.

The resulting reaction solution is put on a 3.6×46 cm column of Amberlite XAD-2 resin prepared in distilled, deionized water; eluting with the same solvent, water. With the flow rate set at 1 drop/sec., individual fractions comprising 200 drops each are collected. Absorbance at 254 nm is observed. Unreacted starting materials 1 and 2 come off first, their departure being signaled by a long minimum in absorbance at 254 nm. When the product begins coming over, the eluting solvent is changed to aqueous 5% tetrahydrofuran (THF). Fractions containing 3 are pooled and lyophylized to yield pure product 3. The pooled fractions are known to contain pure 3 on assay by HPLC, using $C_{18}$ reverse phase column and aqueous 10% THF as the mobile phase.

EXAMPLE 26

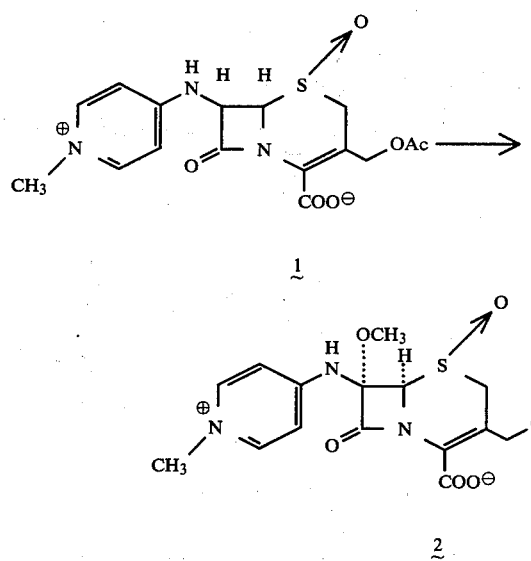

The product of Example 26(1, above), (1.0 mol) is dissolved in anhydrous methanol (1.0 ml) at r.t. (20° C.) and the solution is cooled to −68° C. under an atmosphere of dry N₂ in an acetone/solid CO₂ bath. A solution of lithium methoxide in methanol (1.83 ml, 5.0 mol., of 1.5 N-LiOMe)/MeOH) is added by syringe through a rubber septum to the magnetically stirred solution which at once becomes clear and orange colored. After 2 minutes t-butylhypochlorite (t-BuOCl, 79 μl, density=0.91, 1.2 mol.) is added by syringe as above. Stirring is continued for five minutes at −68° C.; whereupon the reaction is quenched by adding acetic acid (315 μl 10.0 mol). The solution is evaporated at 25° C. under reduced pressure to yield crude 2.

The resulting product is chromatographed in pure distilled water over a 3.1×43 cm. column of Amberlite XAD-2 resin. Initial elution was by water at a flow rate of 2 drops/sec.; individual fractions comprising 400 drops each (~26 ml) are collected. Absorbance at 254 nm is observed. When the product comes down, the solvent is changed to aqueous 5% THF. Fractions comprising 2 are pooled and lyophylized to yield product 2. A 30 mg fraction is purified by preparative reverse phase liquid chromatography to yield the desired product 2.

EXAMPLE 27

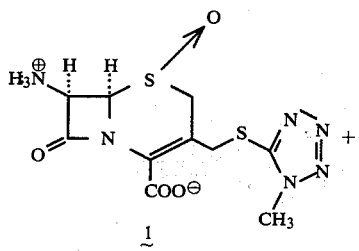

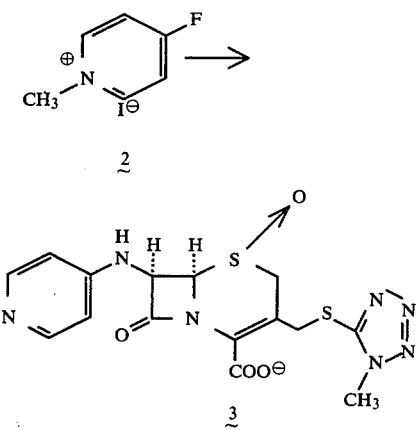

With the end-point set at 7.5 pH, aqueous 1.0 NaOH is added from an automatic burette to a vigorously magnetically stirred suspension of 1. A quantity (175 mg; 0.73 mmole) of 4-fluoro-1-methylpyridinium iodide (2) is dissolved in distilled water (0.5 ml), added in one portion at 20° C. to the above stirred solution. The automatic burette responds at once to maintain pH=7.5.

After 1.0 hour, more pyridinium reagent 2 (43 mg; 0.18 mmole; i.e., 0.91 mmole total) is added directly to the reaction solution; and after 1 hour additional reaction, the entire solution at pH=7.5 is put directly on to a 3.1×45 cm. Amberlite XAD-2 resin column prepared in distilled water.

Initially, distilled water is used as the eluting solvent. The flow rate is adjusted to 4 drops/sec., and individual fractions comprising 400 drops each (26 ml) are collected. Absorbance at 254 nm is observed. When the product starts coming down, the solvent is changed to aqueous 5% THF. Fractions comprising 3 are combined and lyophylized to yield product 3.

EXAMPLE 28

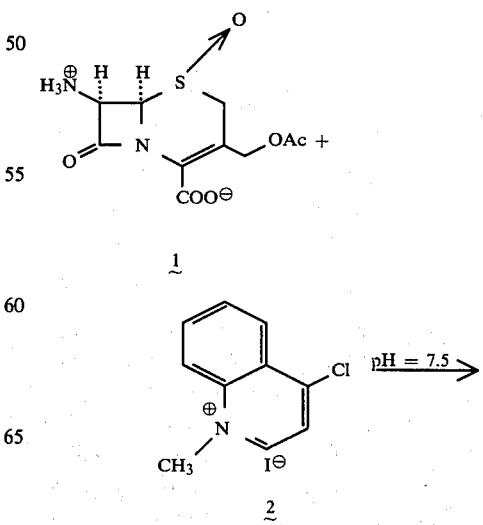

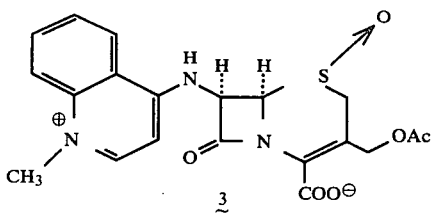

With the end point set at pH=7.5, aqueous NaOH (2.5 N) is added from an automatic burette to a magnetically stirred suspension of 1 (1.836 mmole). The reagent 2, 4-chloro-1-methylquinolinium iodide (0.673 g; 2.203 mmole), is added in one portion to the above solution. Progress of the reaction is monitored by analytical liquid chromatography, using a $C_{18}$ reverse phase column, aq. 10% THF as the mobile phase, and a UV detector. More 4-chloro-1-methylquinolinium iodide (2) (0.55 mmole) is added and stirring at 20°/pH 7.5 continued for a total of 3 hours. Thereafter, the solution is diluted to 40 ml with distilled water and worked up directly by preparative reverse phase liquid chromatography using a 5×30 cm $C_{18}$ column, aq. 2.5%/THF as the mobile phase and a variable wave length UV detector. Fractions comprising 3 are pooled and evaporated at 35° C./0.1 mm to 100 ml then lyophylized yielding (3).

EXAMPLE 29

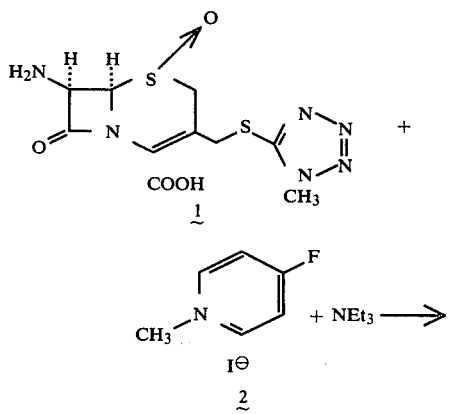

Sieve-dried triethylamine is added to a suspension of 1 (1; 25 gm) in D-DMSO (0.5 ml) at 20° C. The reagent 2, 4-fluoro-1-methylpyridinium iodide (22 mg) is added in one portion reacting instantly. The solution is then shaken with excess of ether (3×2 ml) with decantation. The precipitated product is dried in vacuo to yield the desired product 3.

EXAMPLE 30

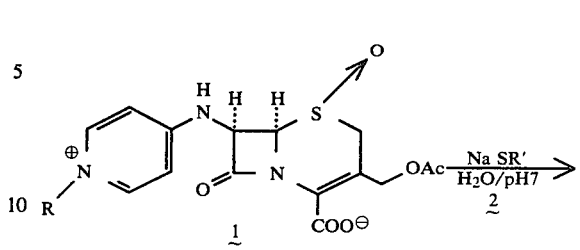

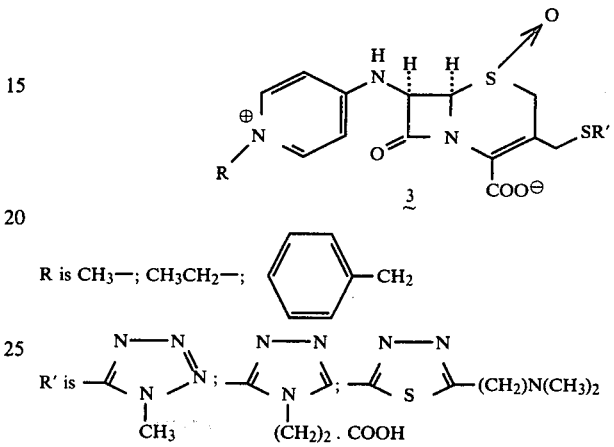

The 3-acetoxymethyl pyridinium cephem (1) (1.0 mmole) is dissolved in water (5–50 ml) at pH 7 containing the alkali metal salt of the heterocyclic thiol 2 (1.0 mmole). This solution is maintained at 25° C. for 2 hours, following the progress of the exchange by analytical L.C. of aliquots over a 0.4×30 cm $\mu C_{18}$ reverse phase column, using a U.V. (254 nm) detector and aqueous THF (5–30%) as mobile phase.

The product 3 is isolated by partition chromatography over Amberlite XAD-2 resin with aqueous THF (0–10%) as mobile phase, monitoring the eluate by analytical L.C. as above. The appropriate fractions are combined, evaporated at 30°/1 mm to small volume (50–100 ml) and lyophilized.

Following the procedure as described, except that the final isolation is accomplished by preparative reverse phase L.C. using $C_{18}$ columns up to 5×30 cm, the appropriate fractions are again combined, evaporated to small volume and lyophilized to provide 3.

EXAMPLE 31

Preparation of

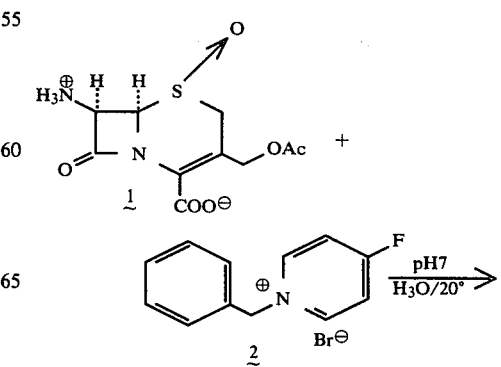

-continued

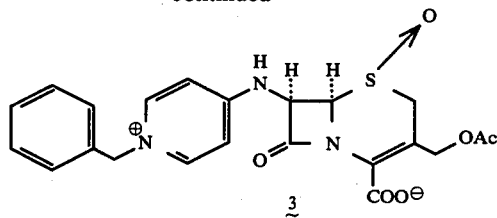

One gram of 1 is suspended in 10 ml. water and dissolved by addition of 1N NaOH from an automatic burette set at a pH of 7. 1-benzyl-4-fluoro-pyridinium bromide, 1.46 grams in 5 ml. of water is added. The pH is maintained at 7. After 2.5 hours the reaction is filtered. The filtrate is washed with EtOAc and cooled to 0° C. overnight. This precipitate is dissolved in methanol, filtered to remove insolubles and concentrated under reduced pressure to a solid. After trituration with dimethylformamide and then ether, a portion of the precipitate is chromatographed in 5% tetrahydrofuran/water on 30–70μ Bondapak reverse phase column. The eluent is concentrated to a small volume and lyophilized yielding 0.151 grams product, 3.

EXAMPLE 32

Preparation of

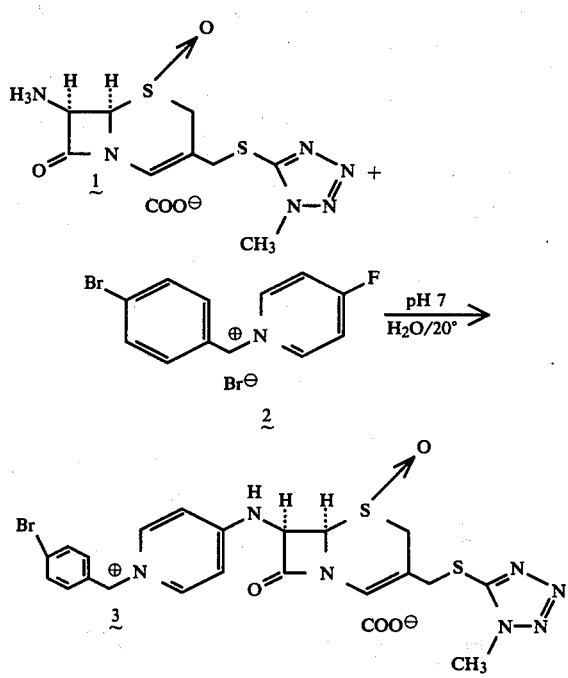

One gram of 1 is supended in water (10 ml) and dissolved by the addition of 1N NaOH from an automatic burette set at a pH of 7.5. The mixture is filtered and the filtrate is added to 2.9 mmoles of 1-(4'-bromobenzyl)-4-fluoropyridinium bromide. The pH is maintained at 7.5 with 1N NaOH. After cessation of base addition, the reaction is complete. The precipitate is isolated by filration and dried. This solid is extensively washed with 100 ml. of methanol to extract the desired product. This methanol solution is concentrated under reduced pressure to a solid which is triturated with water and then acetone. The remaining solid is dissolved in 30% tetrahydrofuran and water, and chromatographed on μC8 Chromegaprep reverse phase column in 3% THF/water. The eluted fractions are concentrated under reduced pressure and lyophilized to yield the desired product, 3.

EXAMPLE 33

Preparation of

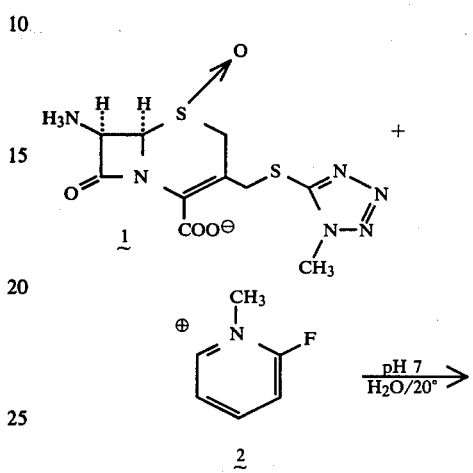

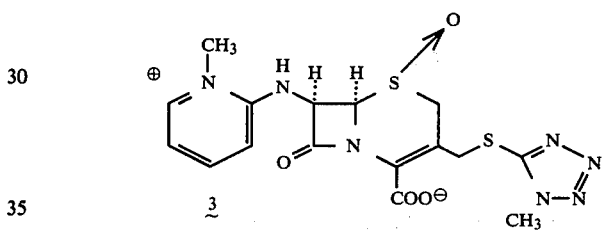

One gram of 1 is suspended in 6 ml. water and dissolved by the addition of 1N NaOH from an automatic burette set at a pH of 7.5. 2-Fluoro-1-methyl-pyridinium iodide, 1.30 grams in 2 ml. of water is added. The pH is maintained at 7.5 with 1N NaOH. After five hours the reaction is diluted with water and washed with five equal portions of ethylacetate. The aqueous phase is filtered and concentrated under reduced pressure to remove remaining EtOAc. The solution is chromatographed on a Waters Prep 500 reverse phase column eluting with 1.25% tetrahydorfuran water and monitoring fractions with a variable wavelength U.V. detector. The fraction comprising 3 is concentrated and lyophilized yielding the desired product.

EXAMPLE 34

Preparation of

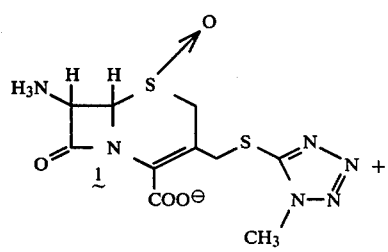

-continued

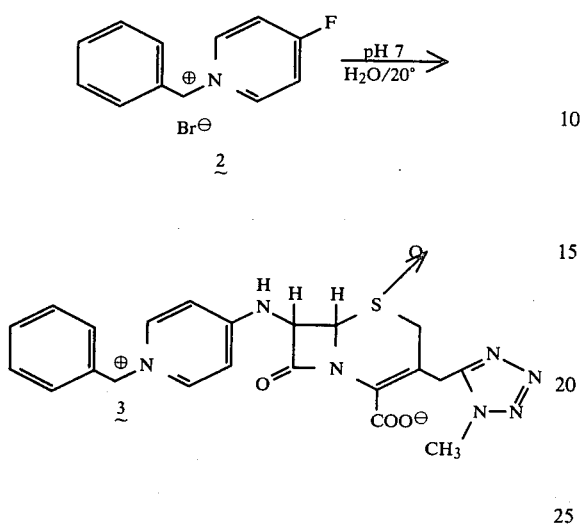

One gram of 1 is suspended in H₂O (10 ml) and dissolved by the addition of 1N NaOH from an automatic burette set at a pH of 7.5. Solid 1-benzyl-4-fluoropyridinium bromide, 1.2 grams, is added. The pH is maintained at 7.5 with 1N NaOH. After two hours the reaction mixture is filtered, washed with water and dried under reduced pressure. The resulting product is washed consecutively with small volumes of H₂O, acetone and ether yielding product, 3.

EXAMPLE 35

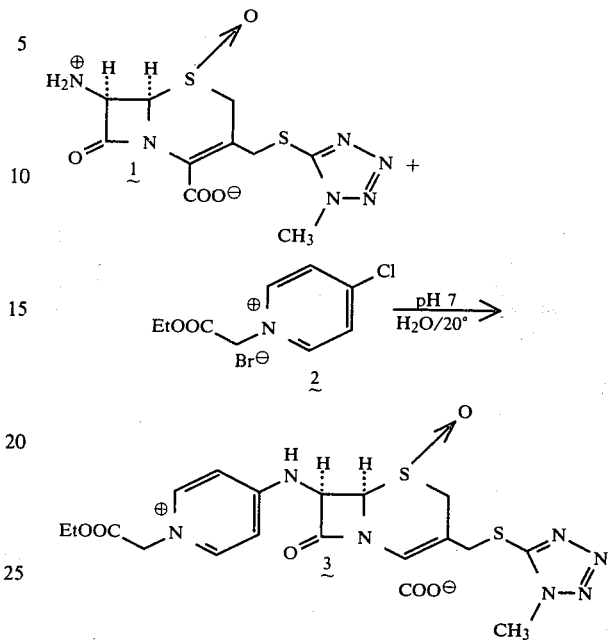

A mixture of (3 mmoles) of 1 in 10 ml. of H₂O is stirred and neutralized to pH 7.4 with 1N NaOH in a pH-stat. A 840 mg. (3 mmoles) sample of 4-chloro-1-carboethoxymethylpyridinium bromide is added and titration continued with 1N NaOh to pH 7.0. Completion of reaction is marked by cessation of base addition.

The reaction solution is washed with three 10-ml. portions of ethyl acetate, diluted to 50 ml. with water and freeze-dried to yield crude product 3.

A 500-mg. portion of the crude product, in 10 ml. of water, is centrifuged. After centrifugation, the supernatant is purified by high performance liquid chromatography. Fractions containing product are concentrated and freeze-dried to yield 3.

EXAMPLE 36

Following the procedure described in the foregoing text and Examples, the following compounds listed in Table I are detailed. In Table I, appropriate remarks are entered to signal any departure from established procedure. Also listed under "Remarks" in Table I are the necessary reagents.

TABLE I

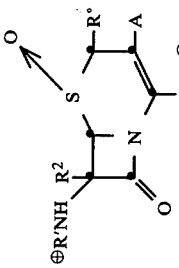

For every entry (compound) in Table I, it is to be understood that
the compounds wherein A is H and R° is either H or CH₃ are also intended.

| Compound | R² | R' | A | Remarks |
|---|---|---|---|---|
| 1 | H | (4-methylpyridinium)-CH₃ | CH₂-S-(1-methyl-tetrazol-5-yl) | (3-fluoro-1-methylpyridinium) I⊖ |
| 2 | H | (4-methylpyridinium)-CH₂CH₃ | " | (3-fluoro-1-ethylpyridinium) BF₄⊖ |
| 3 | H | (4-methylpyridinium)-CH(CH₃)₂ | " | (3-fluoro-1-isopropylpyridinium) ⊖O·SO₂-C₆H₄-CH₃ |
| 4 | H | (4-methylpyridinium)-CH₂CH=CH₂ | CH₂-S-(1-methyl-tetrazol-5-yl) | (3-fluoro-1-allylpyridinium) ⊖O·SO₂-C₆H₄-CH₃ |
| 5 | H | (3,4-dimethyl-1-methylpyridinium) | " | (3-fluoro-2-methyl-1-methylpyridinium) BF₄⊖ |

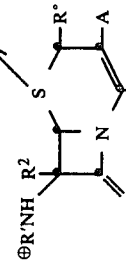

TABLE I-continued

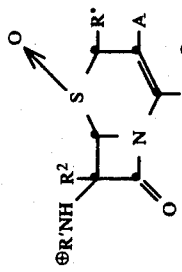

For every entry (compound) in Table I, it is to be understood that the compounds wherein A is H and R° is either H or CH₃ are also intended.

| Compound | R² | R' | A | Remarks |
|---|---|---|---|---|
| 12 | H | pyridinium-CH₃ with COO⊖M⊕ substituent | " | from compound 11 by hydrolysis at pH = 9 then titration to pH = 7 |
| 13 | H | pyridinium-CH₃ with CH₃OOC·CH₂ substituent | triazole with CH₂—S and CH₃ | |
| 14 | H | pyridinium-CH₃ with M⊕⊖OOCCH₂ substituent | " | |
| 15 | H | pyridinium-CH₃ with Cl substituent | " | from compound 13 by hydrolysis at pH = 9 then titration at pH = 7 |
| | | | | pyridinium-CH₃ with F, Cl, CH₃OOC·CH₂, Br⊖ |
| 16 | H | pyridinium-CH₃ with OCH₃ substituent | " | pyridinium-CH₃ with F, OCH₃, BF₄⊖ |

TABLE I-continued

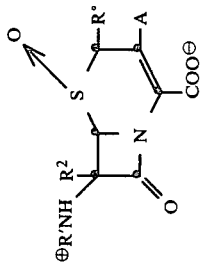

For every entry (compound) in Table I, it is to be understood that the compounds wherein A is H and R° is either H or CH₃ are also intended.

| Compound | R² | R' | A | Remarks |
|---|---|---|---|---|
| 17 | H | (4-methylpyridinium-N-phenyl) | " | (3-fluoropyridinium-N-(4-methylphenyl)) ⊖OSO₂ |
| 18 | H | (4-methylpyridinium-N-benzyl) | " | (3-fluoropyridinium-N-benzyl) Br⊖ |
| 19 | H | (4-methylpyridinium-N-OH) | CH₂—S—(1-methyltetrazolyl) | (3-fluoropyridinium-N-O⊖) |
| 20 | H | (4-methylpyridinium-N-OCH₃) | " | (3-fluoropyridinium-N-OCH₃) BF₄⊖ |
| 21 | H | (4-methylpyridinium-N-NH₂) | " | from compound 8 . by reaction with H₂N . O . SO₃H |

TABLE I-continued
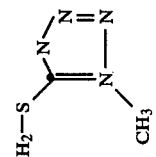
For every entry (compound) in Table I, it is to be understood that the compounds wherein A is H and R° is either H or CH₃ are also intended.
| Compound | R² | R' | A | Remarks |
|---|---|---|---|---|
| 22 | H |  |  |  and subsequent hydrolysis at pH = 9 and titration to pH = 7 |
| 23 | H | 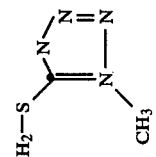 | " |  and subsequent cleavage by CF₃COOH |
| 24 | H |  | " |  and subsequent cleavage by CF₃COOH |
| 25 | H | 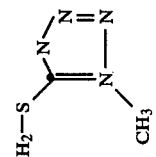 | " |  |

TABLE I-continued

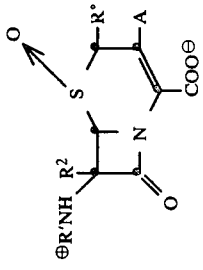

For every entry (compound) in Table I, it is to be understood that the compounds wherein A is H and R° is either H or CH₃ are also intended.

| Compound | R² | R' | A | Remarks |
|---|---|---|---|---|
| 26 | H | ![pyridinium-OH with N-CH₃] | " | from compound 25 by reaction with (a) ISi(CH₃)₃ then (b) H₂O |
| 27 | H | ![pyridinium-OCH₃ with N-CH₃] | " | ![F-pyridinium-OCH₃ N-CH₃ ⊕PF₆] |
| 28 | H | ![pyridone with N-CH₃] | " | from compound 27 by reaction with (a) ISi(CH₃)₃; (b) H₂O; then M⊕OH⊖ to pH 7 isolating the product as the cephem —COO⊖M⊕ |
| 29 | H | ![pyridinium-CH₂OCH₃ with N-CH₃] | " | ![F-pyridinium-CH₂OCH₃ N-CH₃ I⊖] |
| 30 | H | ![pyridinium-CO·NH₂ with N-CH₃] | " | ![F-pyridinium-CO·NH₂ N-CH₃ BF₄⊖] |

TABLE I-continued

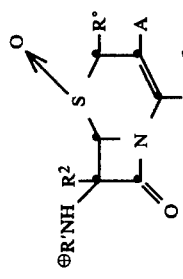

For every entry (compound) in Table I, it is to be understood that the compounds wherein A is H and R° is either H or CH3 are also intended.

| Compound | R² | R' | A | Remarks |
|---|---|---|---|---|
| 31 | H | (4-methyl-2-carbamoyl-N-methylpyridinium) | " | (5-fluoro-2-carbamoyl-N-methylpyridinium BF4⁻) |
| 32 | H | (4-methyl-2-ureido-N-methylpyridinium) | " | (5-fluoro-2-ureido-N-methylpyridinium BF4⁻) |
| 33 | H | (4-methyl-N-acetonylpyridinium) | " | (5-chloro-N-acetonylpyridinium Br⁻) |
| 34 | H | (4-methyl-N-phenacylpyridinium) | " | (5-chloro-N-phenacylpyridinium Br⁻) |
| 35 | H | (4-methyl-N-furfurylpyridinium) | " | (5-chloro-N-furfurylpyridinium Br⁻) |

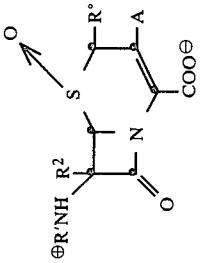

TABLE I-continued $$\overset{\oplus R'NH}{\underset{}{}} \underset{}{\overset{R^2}{\underset{S}{\diagdown}}}\underset{N}{\overset{}{\diagup}}\underset{O}{\overset{R°}{\diagdown}}\underset{COO^\ominus}{\overset{A}{}}$$

For every entry (compound) in Table I, it is to be understood that the compounds wherein A is H and R° is either H or CH₃ are also intended.

| Compound | R² | R' | A | Remarks |
|---|---|---|---|---|
| 41 | H | (2-methylpyridinium-N-yl)methyl-furan | $CH_2-S-$ (1-CH₂CH₂N(CH₃)₂-tetrazol-5-yl) | |
| 42 | OCH₃ | (2-methylpyridinium-N-yl)methyl-furan | $CH_2-S-$ (1-CH₃-tetrazol-5-yl) | from compound 35 by reaction with (a) LiOCH₃ then (b) ClOBuᵗ |
| 43 | OCH₃ | (methylpyridinium-N-yl)methyl-benzene | $CH_2COO^\ominus M^\oplus$ —CH₃ (1-CH₃-tetrazol-5-yl) | from compound 39 by reaction with LiOCH₃ then (b) ClOBuᵗ |
| 44 | H | (3-methyl-pyridinium-N-yl)methyl-4-hydroxybenzene | (3-chloropyridinium-N-yl)methyl-furan Br⊖ | from CH₃CO.O. and subsequent hydrolysis at pH 9 and titration to pH 7 |
| 45 | H | " | $CH_2-S-$ (4-CH₃-thiazol-2-yl); (4-fluoropyridinium-N-yl)methyl-3-acetoxybenzene Br⊖; (4-fluoropyridinium-N-yl)methyl-3-acetoxybenzene Br⊖ | from CH₃CO.O. and subsequent hydrolysis at pH 9 and titration to pH 7 |

TABLE I-continued

For every entry (compound) in Table I, it is to be understood that the compounds wherein A is H and R° is either H or CH₃ are also intended.

| Compound | R² | R' | A | Remarks |
|---|---|---|---|---|
| 46 | H | (3,4-dimethoxybenzyl)-(4-methylpyridinium) | CH₂—S-(1-methyl-tetrazol-2-yl) | (3,4-dimethoxybenzyl)-(4-fluoropyridinium) Br⊖ |
| 47 | H | (benzyl)-(4-methyl-2-carboxypyridinium) | " | (benzyl)-(4-fluoropyridinium) Br⊖ COOCH₃ from compound 47 by hydrolysis at pH 9 then titration to pH 7 |
| 48 | H | (benzyl)-(4-methyl-2-carboxylato pyridinium) M⊕ | CH₂—S-(1-methyl-5-hydroxymethyl-tetrazol-2-yl) | (benzyl)-(4-fluoropyridinium) Br⊖ |
| 49 | H | (benzyl)-(4-methylpyridinium) | CH₂·O·CO·NH₂ | " |
| 50 | H | (benzyl)-(4-methylpyridinium) | CH₂O·COCH₃ | |
| 51 | H | (3-methylsulfinylbenzyl)-(4-methylpyridinium) | | (3-methylsulfonylbenzyl)-(4-fluoropyridinium) Br⊖ |

TABLE I-continued

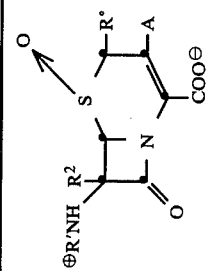

For every entry (compound) in Table I, it is to be understood that the compounds wherein A is H and R° is either H or CH₃ are also intended.

| Compound | R² | R' | A | Remarks |
|---|---|---|---|---|
| 52 | H | ![pyridinium with CH₃, N⊕, I⊖] | CH₂—S—[triazole-N=N with CH₃] | ![pyridinium with CH₃, F, N⊕, I⊖] |
| 53 | H | ![pyridinium with CH₃, CH₃, N⊕, I⊖] | " | ![pyridinium with CH₃, CH₃, F, N⊕, I⊖] |
| 54 | H | ![pyridinium with CH₃, N⊕, CH₃OOC] | " | by reaction in anhydrous DMF with Et₂NPi as base. ![pyridinium with CH₃, F, N⊕, CH₃OOC, BF₄⊖] |
| 55 | H | ![pyridinium with CH₃, N⊕, M⊕OOC] | " | from compound 54 by hydrolysis at pH 9 then titration to pH 7 |
| 56 | H | ![pyridinium with CH₃, CH₃, N⊕, CH₃OOC] | " | ![pyridinium with CH₃, F, N⊕, CH₃OOC, BF₄⊖] |

TABLE I-continued

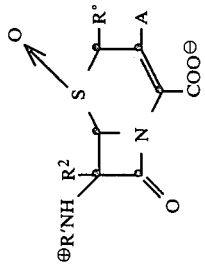

For every entry (compound) in Table I, it is to be understood that the compounds wherein A is H and R° is either H or CH₃ are also intended.

| Compound | R² | R' | A | Remarks |
|---|---|---|---|---|
| 57 | H | (2,6-dimethyl-4-carboxylatopyridinium, M⊕⁻OOC) | " | from compound 56 by hydrolysis at pH 9 then titration to pH 7 |
| 58 | H | (2-fluoro-6-methyl-4-carbamoylpyridinium, H₂NOC, BF₄⊖) | " | |
| 59 | H | (2-methyl-3-chloropyridinium, BF₄⊖) | " | (2-fluoro-6-methyl-3-chloropyridinium, BF₄⊖) |
| 60 | H | (2-methyl-4-chloropyridinium, BF₄⊖) | " | (2-fluoro-6-methyl-4-chloropyridinium, BF₄⊖) |
| 61 | H | (2,6-dimethylpyridinium, BF₄⊖) | " | (2-fluoro-6-methylpyridinium with CH₃, BF₄⊖) |

TABLE I-continued

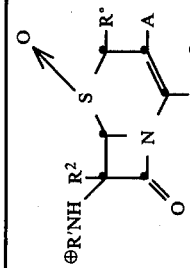

For every entry (compound) in Table I, it is to be understood that the compounds wherein A is H and R° is either H or CH₃ are also intended.

| Compound | R² | R' | A | Remarks |
|---|---|---|---|---|
| 62 | H | CH₃.O.CH₂—N⊕(pyridinium) | CH₃.O.CH₂—N⊕F(pyridinium)Br⊖ | |
| 63 | H | H—N⊕(pyridinium) | " | from compound 62 by reaction with (a) ISi(CH₃)₃ then (b) H₂O |
| 64 | H | HO—N⊕(pyridinium) | " | |
| 65 | H | CH₃O—N⊕(pyridinium) | " | BF₄⊖ CH₃O—N⊕F(pyridinium) |
| 66 | H | NH₂—N⊕(pyridinium) | " | from compound 63 by reaction with H₂NO.SO₃H |
| 67 | H | CHOOC.CH₂—N⊕(pyridinium) | " | CH₃OOC.CH₂—N⊕F(pyridinium)Br⊖ |

TABLE I-continued
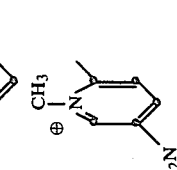
For every entry (compound) in Table I, it is to be understood that the compounds wherein A is H and R° is either H or CH₃ are also intended.
| Compound | R² | R' | A | Remarks |
|---|---|---|---|---|
| 68 | H | 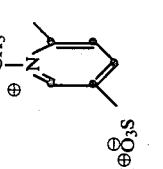 | " | from compound 67 by hydrolysis at pH 9 then titration to pH 7 |
| 69 | H | 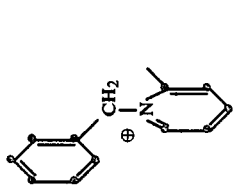 | " | 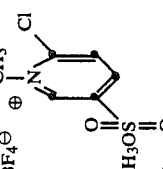 Bu'O . CONH and subsequent cleavage by CF₃ . COOH |
| 70 | H | 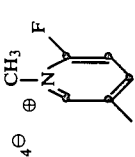 | " | 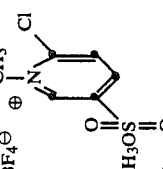 |
| 71 | H | 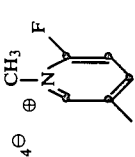 | " | and subsequent hydrolysis at pH 9 and titration to pH 7 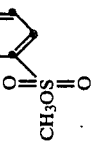 |

TABLE I-continued

For every entry (compound) in Table I, it is to be understood that the compounds wherein A is H and R° is either H or CH₃ are also intended.

| Compound | R² | R' | A | Remarks |
|---|---|---|---|---|
| 72 | H | (4-HO-phenyl)-CH₂-N⁺(2-CH₃-pyridinium) | " | |
| 73 | H | (4-CH₃OOC-phenyl)-CH₂-N⁺(2-CH₃-pyridinium) | " | FROM CH₃COO and subsequent hydrolysis at pH 9 and titration to pH 7 |
| 74 | H | (3-M⁺⁺OOC-phenyl)-CH₂-N⁺(2-CH₃-pyridinium) | " | (4-CH₃OOC-phenyl)-CH₂-N⁺(2-F-pyridinium) Br⁻ from compound 73 by hydrolysis at pH 9 then titration to pH 7; (3-CH₃OOC-phenyl)-CH₂-N⁺(2-F-pyridinium) Br⁻ |

TABLE I-continued

For every entry (compound) in Table I, it is to be understood that the compounds wherein A is H and R° is either H or CH₃ are also intended.

| Compound | R² | R' | A | Remarks |
|---|---|---|---|---|
| 75 | H | furfuryl-N-(2-methylpyridinium) | " | furfuryl-N-(2-fluoropyridinium) Br⊖ |
| 76 | H | N-methyl-2-methylpyridinium I⊖ | CH₂-S-(tetrazolyl-CH₂-COO⊖M⊕) | N-methyl-2-fluoropyridinium I⊖ |
| 77 | OCH₃ | N-methyl-2-methylpyridinium | " | from compound 76 by reaction with (a) LiOCH₃ then (b) ClOBuᵗ |
| 78 | H | benzyl-N-(2-methylpyridinium) | " | benzyl-N-(2-fluoropyridinium) Br⊖ |

TABLE I-continued

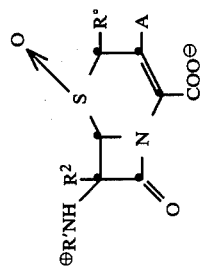

For every entry (compound) in Table I, it is to be understood that the compounds wherein A is H and R° is either H or CH₃ are also intended.

| Compound | R² | R' | A | Remarks |
|---|---|---|---|---|
| 79 | H | [furan-CH₂-N⁺-pyridinium with CH₃, Br⁻] | [CH₂-S-triazole-CH₂COO⁻ M⁺] | [furan-CH₂-N⁺-pyridinium with F, Br⁻] |
| 80 | OCH₃ | [furan-CH₂-N⁺-pyridinium, Br⁻] | " | from compound 79 by reaction with (a) LiOCH₃ then (b) ClOBu$^t$ |
| 81 | H | [dichlorophenyl-CH₂-N⁺-pyridinium with CH₃] | [CH₂-S-triazole-CH₂CH₂SO₃⁻ M⁺] | [dichlorophenyl-CH₂-N⁺-pyridinium with F, Br⁻] |

TABLE I-continued
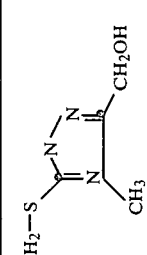
For every entry (compound) in Table I, it is to be understood that the compounds wherein A is H and R° is either H or CH₃ are also intended.
| Compound | R² | R' | A | Remarks |
|---|---|---|---|---|
| 82 | H | 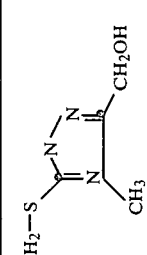 | 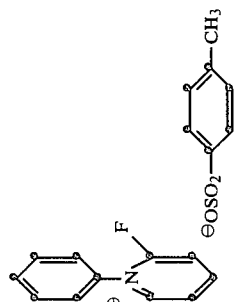 | 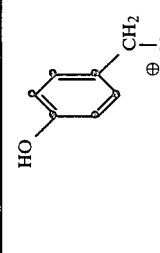 |
| 83 | H | 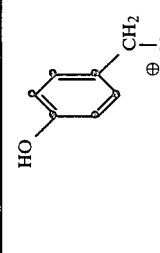 | $CH_2O \cdot CO \cdot NH_2$ | and subsequent hydrolysis at pH 9 and titration to pH 7  |
| 84 | H | 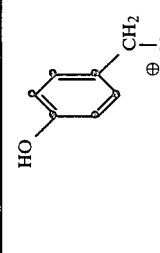 | 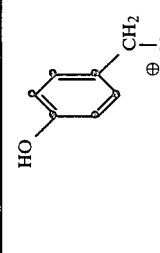 |  |

TABLE I-continued
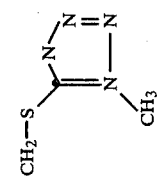
For every entry (compound) in Table I, it is to be understood that the compounds wherein A is H and R° is either H or CH₃ are also intended.
| Compound | R² | R' | A | Remarks |
|---|---|---|---|---|
| 85 | H |  | 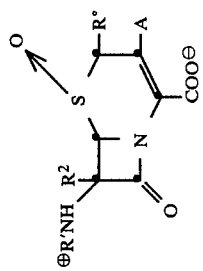 | from compound 84 by hydrolysis at pH 9 then titration to pH 7 |
| 86 | H |  | " | |
| 87 | H | | " | from compound 86 by hydrolysis at pH 9 then titration to pH 7 |

TABLE I-continued
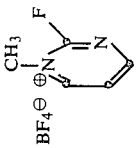
For every entry (compound) in Table I, it is to be understood that the compounds wherein A is H and R° is either H or CH₃ are also intended.
| Compound | R² | R' | A | Remarks |
|---|---|---|---|---|
| 88 | H | 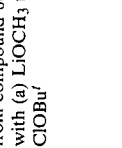 | " | BF₄⁻ 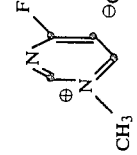 |
| 89 | OCH₃ | (same structure) | " | from compound 88 by reaction with (a) LiOCH₃ then (b) ClOBuᵗ |
| 90 | H | CH₂.CH₃ structure | " | CH₂.CH₃ structure |
| 91 | H | structure | " | BF₄⁻ structure |
| 92 | H | structure | " | ⁻OSO₂-C₆H₄-CH₃ structure |

TABLE I-continued
For every entry (compound) in Table I, it is to be understood that the compounds wherein A is H and R° is either H or CH$_3$ are also intended.
| Compound | R$^2$ | R' | A | Remarks |
|---|---|---|---|---|
| 93 | H | 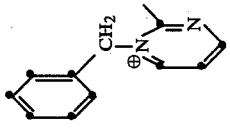 | 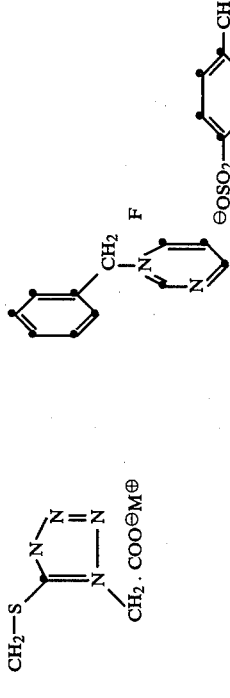 | |
| 94 | H | 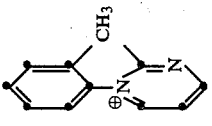 | 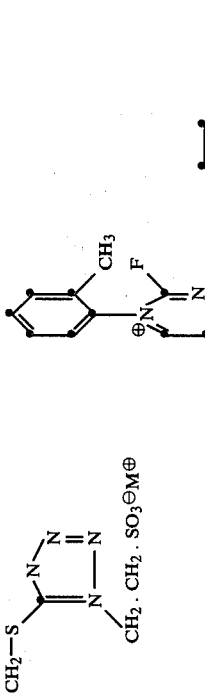 | from compound 92 by reaction with (a) LiOCH$_3$ then (b) ClOBu$^t$ |
| 95 | OCH$_3$ |  | " | |
| 96 | H | 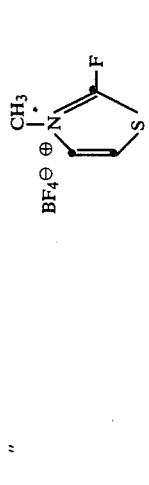 | " | |

TABLE I-continued

For every entry (compound) in Table I, it is to be understood that the compounds wherein A is H and R° is either H or CH₃ are also intended.

| Compound | R² | R' | A | Remarks |
|---|---|---|---|---|
| 97 | H | [3-phenyl-4-methyl-thiazolium] | [CH₂S-tetrazole-CH₂COO⁻M⁺] | BF₄⁻ |
| 98 | H | [2-methyl-3-ethyl-thiazolium] | [CH₂S-thiazole-SCH₂COO⁻M⁺] | BF₄⁻ |
| 99 | OCH₃ | [2-methyl-3-ethyl-thiazolium] | " | from compound 98 by reaction with (a) LiOCH₃ then (b) ClOBuᵗ |
| 100 | H | [5-phenyl-3-ethyl-4-methyl-isoxazolium] | " | BF₄⁻, [5-phenyl-3-ethyl-4-fluoro-isoxazolium] |
| 101 | H | [3-ethyl-4-methyl-isoxazolium] | [CH₂S-triazole-CH₃] | BF₄⁻, [3-ethyl-4-fluoro-5-methyl-isoxazolium] |

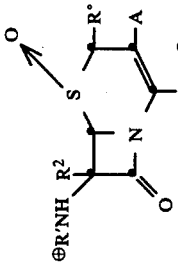

TABLE I-continued

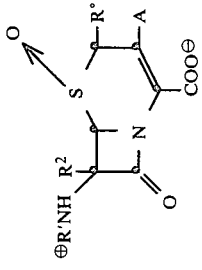

For every entry (compound) in Table I, it is to be understood that the compounds wherein A is H and R° is either H or CH₃ are also intended.

| Compound | R² | R' | A | Remarks |
|---|---|---|---|---|
| 107 | OCH₃ | [benzimidazolium with CH₃O, N-CH₃, N-CH₃] | [methylthio-methyl-triazole: CH₂—S—C(N=N-N-CH₃)] | from compound 106 by reaction with (a) LiOCH₃ then (b) ClOBuᵗ |
| 108 | H | [benzoxazolium, N-CH₂CH₃] | " | BF₄⁻ |
| 109 | H | [benzoxazolium, N-CH₃] | " | BF₄⁻ |
| 110 | H | [benzothiazolium, N-CH₃] | " | BF₄⁻ |
| 111 | H | [isocyano-methylpyridinium] | " | [tolyl-OSO₂⁻ with isocyano-fluoropyridinium] |

TABLE I-continued

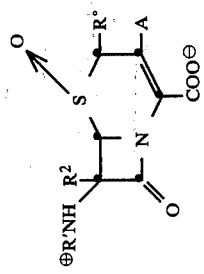

For every entry (compound) in Table I, it is to be understood that the compounds wherein A is H and R° is either H or CH₃ are also intended.

| Compound | R² | R' | A | Remarks |
|---|---|---|---|---|
| 112 | H | (pyridinium with CN, 2-methyl) | " | (pyridinium-CN, F) ⁻OSO₂-C₆H₄-CH₃ |
| 113 | H | (methylpyridinium) | " | (F-pyridinium) Br⁻ |
| 114 | H | (methylpyridinium-CH₃) | " | (F-pyridinium-CH₃) Br⁻ |
| 115 | H | (pyrrolizinium) | " | (F-pyrrolizinium) ClO₄⁻ |
| 116 | H | (methylpyrrolizinium) | " | (F-pyrrolizinium) ⁻OSO₂-C₆H₄-CH₃ |

TABLE I-continued

For every entry (compound) in Table I, it is to be understood that the compounds wherein A is H and R' is either H or CH₃ are also intended.

| Compound | R² | R' | A | Remarks |
|---|---|---|---|---|
| 117 | H | (pyrrolidinium ring) | (fluoropyridinium with OSO₂-tolyl) | |
| 118 | H | (pyridinium ring) | Br⁻ | |
| 119 | OCH₃ | (pyridinium ring) | CH₃—S— (tetrazole with CH₂COO⁻M⁺) | " |
| 120 | H | (N-benzylpyridinium) | CH₂.O.CO.CH₃ | from compound 118 by reaction with (a) LiOCH₃ then (b) ClOBuᵗ |
| 121 | H | (N-benzylpyridinium) | CH₂—⁺N(pyridinium-CO.CH₃)  ⁻O.CO.CH₃ | (3-fluoro-N-benzylpyridinium) Br⁻ from compound 120, by reaction with (pyridine) in aqueous solution |
| 122 | H | (N-benzylpyridinium) | CH₂—⁺N(pyridinium-CONH₂)  ⁻O.CO.CH₃ | from compound 120 by reaction with (nicotinamide) —CO.NH₂ in aqueous solution |

TABLE I-continued

For every entry (compound) in Table I, it is to be understood that the compounds wherein A is H and R' is either H or CH₃ are also intended.

| Compound | R² | R' | A | Remarks |
|---|---|---|---|---|
| 123 | OCH₃ | 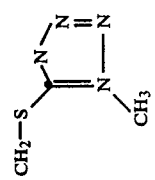 | CH₂.O.CO.CH₃ | from compound 120 by reaction with (a) LiOCH₃ then (b) ClOBu$^t$ |
| 124 | OCH₃ | " | 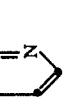 | from compound 123 by reaction with 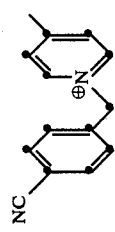 CO.NH₂ in aq. solution |
| 125 | H | 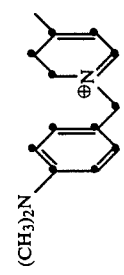 | 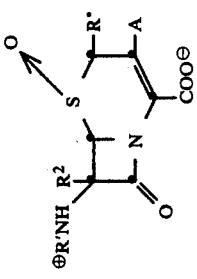 | |
| 126 | H |  | " | prepared from compound 125 by reaction with (a) ISi(CH₃)₃ then (b) H₂O |
| 127 | H |  | " |  |
| 128 | H |  | " |  |

TABLE I-continued
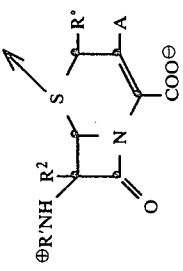
For every entry (compound) in Table I, it is to be understood that
the compounds wherein A is H and R° is either H or CH₃ are also intended.
| Compound | R² | R' | A | Remarks |
|---|---|---|---|---|
| 129 | H | | " | |
| 130 | H | Cl₃C . CH₂ . O . CH₂—⊕N | | |
| 131 | H | Cl₃C . CH₂ . OCH₂—⊕N | —CH₂S | OTs |
| 132 | H | " | | Cl₃C . CH₂ . OCH₂—⊕N Br⊖ |
|  |  |  | —CH₂—S | " Cl₃C . CH₂ . OCH₂—⊕N Br⊖ |
|  |  |  | —CH₂—S S . CH₂ . COO⊖Na⊕ | |

EXAMPLE 37

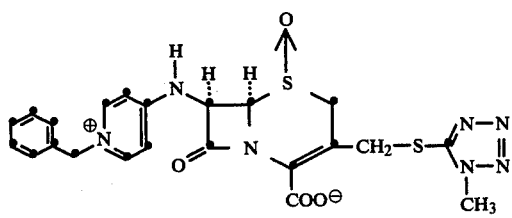

Preparation of Pharmaceutical Compositions

One such unit dosage form comprises a blend of 120 mg of 1 with 20 mg of lactose and 5 mg of magnesium stearate which is placed in a No. 3 gelatin capsule. Similarly, by employing more of the active ingredient and less lactose, other dosage forms can be prepared; should it be necessary to mix more than 145 mg. of ingredients together, larger capsules may be employed. Equivalently, compressed tablets and pills can be prepared. The following examples are further illustrative of the preparation of pharmaceutical formulations:

| TABLET | PER TABLET |
|---|---|
| 1 | 125 mg. |
| Dicalcium Phosphate | 200 mg. |
| Cornstarch, U.S.P. | 6 mg. |
| Lactose, U.S.P | 200 mg. |
| Magnesium Stearate | 270 mg. |

The above ingredients are combined and the mixture is compressed into tablets, approximately 0.5 inch in diameter each weighing 800 mg.

What is claimed is:

1. A compound having the structural formula:

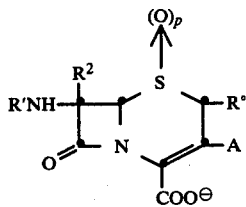

and the pharmaceutically acceptable salts and esters thereof wherein: p is 1 or 2; R° is H or CH$_3$; R$^2$ is hydrogen or methoxyl; R' is selected from the group consisting of:

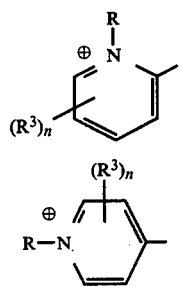 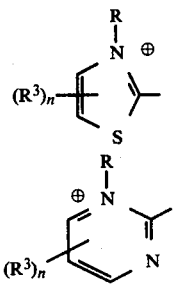

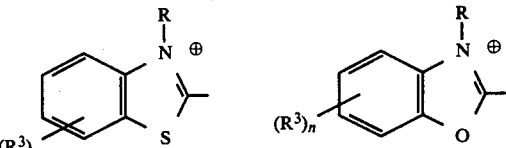
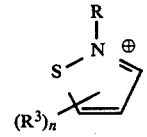 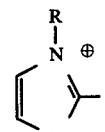
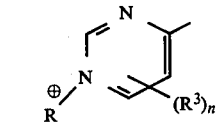 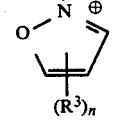
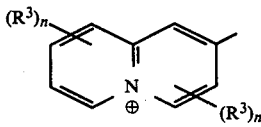 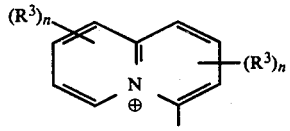
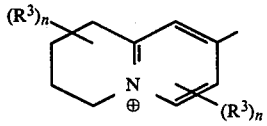 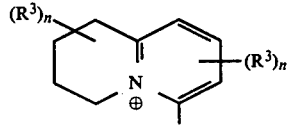
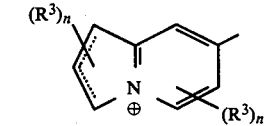 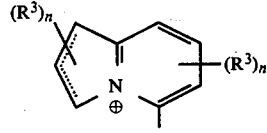

wherein the dotted line indicates both saturated and unsaturated rings; and wherein:

R is hydrogen alkyl having from 1-6 carbon atoms, substituted alkyl having from 1-6 carbon atoms wherein the substituent is chloro, fluoro, hydroxyl, alkoxyl (C$_{1-6}$), carboxyl, amino, sulfo and mono- and dialkylamino wherein each alkyl has 1-6 carbon atoms substituted and unsubstituted phenylaklkyl and phenylalkenyl having 7-12 carbon atoms wherein the substituent is selected from chloro, fluoro, carboxyl, amino, cyano, hydroxyl and sulfo;

R$^3$ is chloro, fluoro, hydroxyl, carboxyl, sulfo, cyano, amino, mono- and dialkylamino, alkoxyl, alkyl having from 1-6 carbon atoms, substituted alkyl having 1-6 carbon atoms wherein the substituent is carboxyl, cyano, alkoxyl having 1-6 carbon atoms, phenyl and phenyloxy;

n is an integer selected from 0 to 3 and

A is selected from:

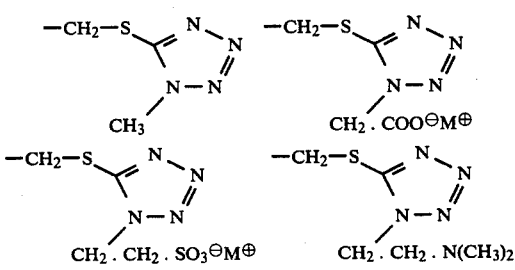

-continued

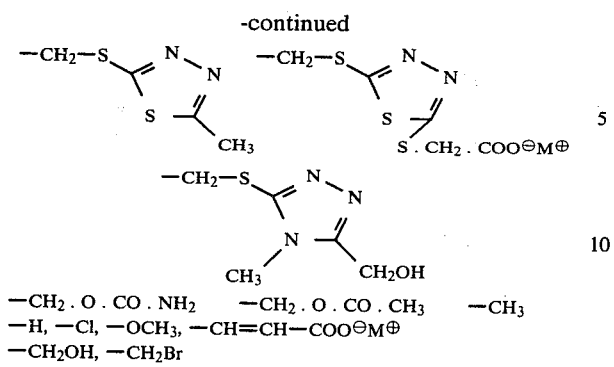

—CH₂.O.CO.NH₂  —CH₂.O.CO.CH₃  —CH₃
—H, —Cl, —OCH₃, —CH=CH—COO⁻M⁺
—CH₂OH, —CH₂Br

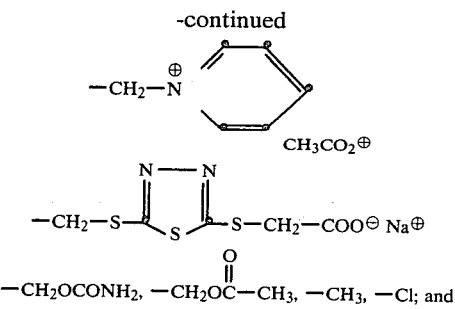

wherein Y is a pharmaceutically acceptable anion and M is a pharmaceutically acceptable cation.

2. A compound according to claim 1 wherein A is hydrogen.

3. A compound according to claim 1 wherein p=1.

4. A compound according to claim 1 wherein n is 0 or 1; R is hydrogen or substituted or unsubstituted alkyl or phenylalkyl; p is 1; and R° is H.

5. A compound according to claim 1 wherein n is 0 or 1; R is H or substituted or unsubstituted alkyl or phenylalkyl; p is 1; and A is H.

6. A compound according to claim 4 wherein
A is selected from the group consisting of: hydrogen,

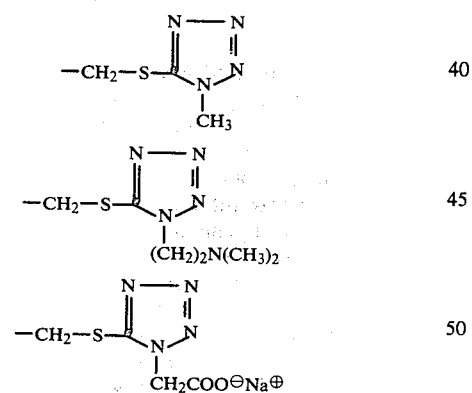

-continued

—CH₂—N⁺⟨pyridine⟩ CH₃CO₂⁻

—CH₂—S—⟨thiadiazole⟩—S—CH₂—COO⁻ Na⁺

—CH₂OCONH₂, —CH₂OC(=O)—CH₃, —CH₃, —Cl; and

R' is selected from:

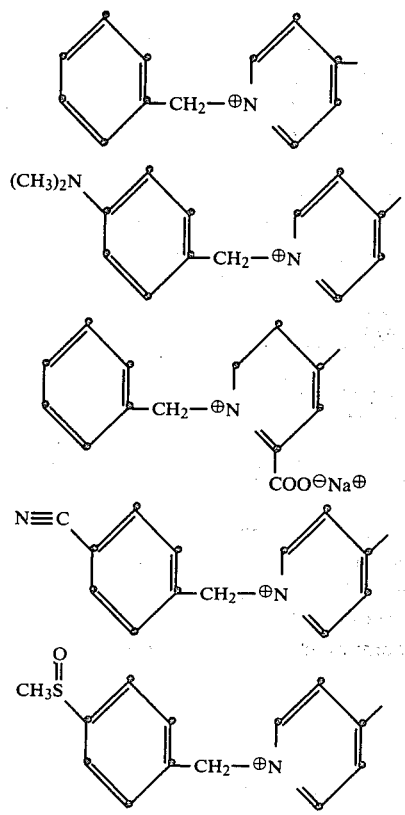

7. An antibiotic pharmaceutical composition comprising a therapeutically effective amount of a compound according to claim 1 and a pharmaceutical carrier therefor.

* * * * *